United States Patent [19]

Piwinski et al.

[11] Patent Number: 4,666,906
[45] Date of Patent: May 19, 1987

[54] COMPOUNDS FOR TREATING HYPERTENSION

[75] Inventors: John J. Piwinski, Parsippany, N.J.; John T. Suh, Greenwich, Conn.; Paul Menard, Tuckahoe, N.Y.; Howard Jones, Holmdel, N.J.; Edward S. Neiss, New Canaan, Conn.; John R. Regan, Mamaroneck, N.Y.

[73] Assignee: USV Pharmaceutical Corporation, Fort Washington, Pa.

[21] Appl. No.: 756,530

[22] Filed: Jul. 19, 1985

Related U.S. Application Data

[63] Continuation-in-part of Ser. No. 690,387, Jan. 10, 1985, Pat. No. 4,596,791, which is a continuation of Ser. No. 475,804, Mar. 16, 1983, abandoned.

[51] Int. Cl.$^4$ .................... A61K 31/54; C07D 285/22
[52] U.S. Cl. ........................................ 514/222; 544/12
[58] Field of Search .................. 514/19, 222; 530/800; 260/998.2; 544/12

[56] References Cited

U.S. PATENT DOCUMENTS

| | | | |
|---|---|---|---|
| 4,350,704 | 9/1982 | Hoefle et al. | 424/274 |
| 4,370,494 | 1/1983 | Wright et al. | 562/450 |
| 4,374,829 | 2/1983 | Harris et al. | 514/19 |
| 4,474,692 | 10/1984 | Oka et al. | |
| 4,482,544 | 11/1984 | Huang et al. | |
| 4,496,542 | 1/1985 | Skiles et al. | 514/2 |
| 4,596,791 | 6/1986 | Piwinski et al. | 514/19 |

FOREIGN PATENT DOCUMENTS 0050800  5/1982  European Pat. Off. .
2095682 10/1983  United Kingdom .

OTHER PUBLICATIONS

Tetrahedron Letters, vol. 23, No. 39, 3995–3998 (1982).
Bull. Chem. Soc., Jpn. 53, 3661–3669 (1980).
Biochem. and Biophys. Res. Commun. (1981) 963–969, vol. 102, No. 3.

Primary Examiner—Delbert R. Phillips

[57] ABSTRACT

Compounds of the formula

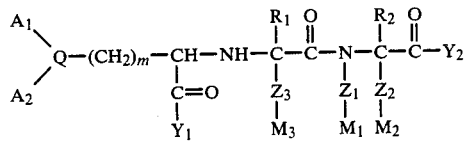

and their pharmaceutically acceptable salts, wherein the substituents are as defined herein, having antihypertensive activity.

6 Claims, No Drawings

COMPOUNDS FOR TREATING HYPERTENSION

BACKGROUND OF THE INVENTION

This application is a continuation-in-part of application Ser. No. 690,387, filed Jan. 10, 1985 U.S. Pat. No. 4,596,791, which is a continuation of application Ser. No. 475,804, filed Mar. 16, 1983 now abandoned.

This application relates to compounds, their pharmaceutically acceptable salts, and pharmaceutical preparations made therefrom, having utility in the treatment of hypertension in subjects suffering therefrom.

SUMMARY OF THE INVENTION

Broadly stated, the present invention comprises compounds of the formula

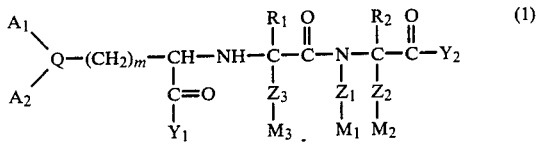

and pharmaceutically acceptable salts thereof, wherein
$A_1$ and $A_2$ are independently hydrogen, halogen, hydroxy, alkyl, alkoxy, or trifluoromethyl;
Q is phenyl or fused arylcycloalkyl;
m is 0 to 3 inclusive;
$Y_1$ and $Y_2$ are independently —OR or

$R_1$ and $R_2$ are independently R, cycloalkyl, or aminoalkyl,
wherein
$Z_1$, $Z_2$, and $Z_3$, reading toward the $M_i$ substituent, are selected from the group consisting of -(alk)-, —N(R)-(alk)-, —N(R)(alk)N(R)—,

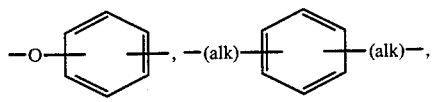

—N(R)—(CHR$_3$)-(alk)-N(R)—C(O)—, -(alk)-SO$_2$—, -(alk)-N(R)SO$_2$—, -(alk)-S-(alk)-, -(alk)-O-(alk)-, -)alk)-N(R)—, -(alk)-N(R)C(O), -(alk)-C(O)N(R)—, -(alk)-C(O)—, or -(alk)-N(R)—C(O)O—, wherein alk represents a straight alkyl chain of formula —($C_nH_{2n}$)—, or an alkyl chain of formula —($C_nH_{2n-1}$)— which is substituted with a straight or branched alkyl group having 1 to 4 carbon atoms, in which n in each occurrence is 0 to 6 inclusive,
$M_1$, $M_2$, and $M_3$ are independently selected from the group consisting of hydrogen, alkyl, cycloalkyl, aryl, fused polycyclic aryl, or fused cycloalkylaryl, wherein up to 3 carbon atoms of $M_1$, $M_2$ and M;hd 3 can be oxidized to -C(O)- or replaced by —NH—, —O—, —S—, =N—, or —SO$_2$—; wherein each of $M_1$, $M_2$ and $M_3$ is unsubstituted or has up to three substituents selected from the group consisting of halogen, alkyl, aminoalkyl, aralkyl, cycloalkyl, nitroalkylamino, acylamino, acylaminoalkyl, acylaminoalkylamino, trifluoromethyl, nitro, cyano, —OR, —SR, —C(O)OR, —S(O)R, —SO$_2$R,

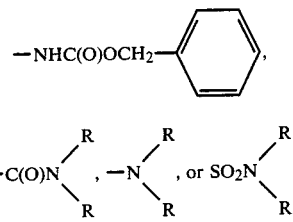

wherein $M_3$ is aryl, fused polycyclic aryl, or fused cycloalkylaryl, and is substituted, $Z_1M_1$ and $Z_2M_2$ can be linked together to form an alkylene bridge up to 6 carbon atoms in length which is optionally substituted with lower alkyl or fused with an aryl ring;
wherein in each occurrence R is independently hydrogen, alkyl, cycloalkyl, aryl, aralkyl, heteroalkyl, heteroaralkyl, or heteroaryl;
$R_3$ is hydrogen or alkyl;
provided that at least one of $M_1$, $M_2$ and $M_3$ is an aryl ring, or has an aryl moiety, in which the aryl ring or moiety has two or three substituents other than hydrogen;
wherein the alkyl groups and the alkyl moieties contain up to 9 carbon atoms, the cycloalkyl groups and moieties are saturated or unsaturated and contain 3 to 12 atoms, and the aryl rings contain up to 12 atoms.

DESCRIPTION OF THE PREFERRED EMBODIMENTS

Preferred compounds of the present invention include those of the general formula given above in which $Y_1$ and $Y_2$ are each hydroxy, benzyloxy, or lower alkoxy; $R_1$ and $R_2$ are each hydrogen, alkyl, aryl, aralkyl, cycloalkyl, or w-amino ("omega-amino")alkyl wherein the amino is mono- or disubstituted with hydrogen, alkyl, aryl, or aralkyl, or is incorporated in a saturated or unsaturated one- or two-ring heterocyclic moiety containing preferably up to 12 atoms in the ring; m is 1 or 2; $A_1$ and $A_2$ are hydrogen or lower alkyl; and Q is phenyl or indanyl.

The alkyl groups per se and the alkyl moieties in alkoxy, aralkyl, cycloalkyl, aminoalkyl, and the like, may be straight-chained or branched and preferably contain from 1 to 9 carbon atoms. Such groups include methyl, ethyl, propyl, isopropyl, butyl, isobutyl, tertiary-butyl, amyl, iso-amyl, hexyl, octyl, and the like. Preferably the alkyl groups are lower alkyl, which term shall refer to alkyl groups containing from 1 to 6 carbon atoms, straight-chained or branched. The cycloalkyl groups and moieties are saturated or unsaturated and contain 3 to 12 carbon atoms and preferably 3 to 9 carbon atoms. "Acyl" is preferably alkanoyl with 2 to 12 carbon atoms.

Preferred structures include those in which $Z_1$, $Z_2$ and/or $Z_3$ is a chemical bond, so that at least one component M is connected directly to the rest of the molecule, and those within the above general definition in which n is 0 (i.e. chemical bond), 1, 2, 3, or 4, and R is hydrogen or lower alkyl.

Preferred structures for the $M_1$, $M_2$ and $M_3$ groups include hydrogen, cycloalkyl, alkyl, aryl, fused arylcycloalkyl, heteroaryl, and fused aryl-heterocycloalkyl.

Preferred cyclic and polycyclic ring structures, including those falling within the definition of $M_1$, $M_2$, and $M_3$, contain up to 20 carbon atoms and include such radicals as cyclopropyl, cyclobutyl, cyclopentyl, cyclohexyl, cycloheptyl, adamantyl, norbornyl, phenyl, tolyl, benzyl, phenethyl, indolyl, hydroxybenzyl, indanyl, naphthyl, tetrahydronaphthyl, decanhydronaphthyl, pyridyl, quinolyl, isoquinolyl, guanidino, pyrrolidyl, pyrrolyl, morpholinyl, furyl, furfuryl, tetrahydrofurfuryl, benzimidazolyl, thienyl, imidazolyl, tetrahydroisoquinolyl,

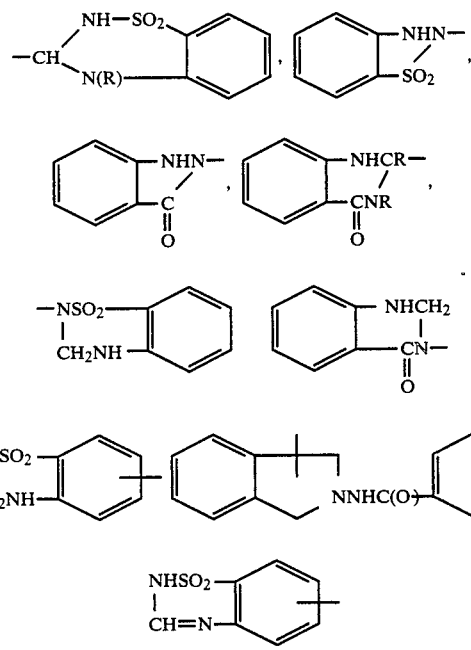

and the like, specifically including all isomers of radicals named herein that have more than one isomer. The cycloalkyl, aryl, and fused aryl-cycloalkyl structures can also contain one or more, preferably up to three, hetero atoms, i.e., sulfur, oxygen, or nitrogen atoms, thereby forming a hetero-ring.

At least one, and preferably one, of $M_1$, $M_2$ and $M_3$ is aryl or has an aryl moiety, in which the aryl group or moiety carries two or three substituents other than hydrogen. Such an Mi group is preferably connected to the main chain by one of the following chains: —NH—C(O)—M; —(CH$_2$)$_4$NH—M; —NH—M; —(CH$_2$)$_4$NHC(O)—M; —CH$_2$C(O)NH—M; —(C$_2$H$_4$)NH—M; —CH$_2$—M; —(CH$_2$)$_3$—M; —NH—NH—C(O)—M; —NH—SO$_2$M; —CH(CH$_2$CH$_3$)CH$_2$NH—M; —N(CH$_3$)-CH$_2$M; —OCH$_2$CH$_2$M; —N(CH$_3$)—M; —CH(CH$_3$)—C(O)NH—M; —CH(CH$_3$)—(CH$_2$)$_3$NH—M; —CH(M); —CH(—CH(CH$_3$)$_2$)—M; —(CH$_2$)$_4$NHC(O)OM; or

More preferred are those chains which form non-labile bonds, so that the molecule (1) resists cleavage in the stomach and is thus intact when it enters the blood, which enhances the therapeutic effect and duration of the compound and may reduce undesirable side-effects.

Structures having an aryl moiety include aryl containing one or more hetero atoms, polycyclic aryl, polycyclic aryl containing one or more hetero atoms, fused arylcycloalkyl, and fused arylcycloalkyl containing one or more hetero atoms. Preferred structures include those in the above list of cyclic and polycyclic structures which have an aryl ring of six carbon atoms. Preferred substituents for the aryl ring include halogen, nitro, lower alkyl, —COOH, carboxy-lower alkoxy, phenoxy, and hydroxy; sulfamoyl which is optionally substituted with alkyl; and amino which is optionally substituted with lower alkyl, phenyl, phenyl-lower alkyl, heteroaryl-lower alkyl, nitro-lower alkyl, lower alkyl-carbonyl, and lower alkyl-carbonyl-aminoalkyl, (e.g., CH$_3$C(O)NH(CH$_2$)$_{2-4}$NH—, CH$_3$C(O)NH—, and furfurylamino).

When $M_3$ has a substituted aryl moiety, —Z$_1$M$_1$ and —Z$_2$M$_2$ can be linked to form an alkylene (i.e. —(CH$_2$)$_n$—) bridge 3, 4, 5 or 6 carbon atoms in length. Preferably the alkylene bridge forms a proline ring with the nitrogen and carbon atoms to which Z$_1$ and Z$_2$ are respectively attached. The alkylene bridge is optionally substituted with lower alkyl. The alkylene bridge can also be fused with an aryl ring; a preferred example is where —Z$_1$M$_1$ and —Z$_2$M$_2$ form a tetrahydroisoquinoline ring, i.e.,

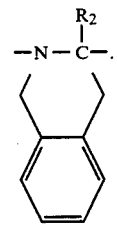

In notation such as

in which R is written twice we intend to indicate that each R can be any of the substituents listed hereinabove for R.

The halo groups include fluoro, chloro, bromo and iodo. Preferred hetero atoms are S, O, and N. Preferred acyl groups are lower alkyl-carbonyl, and aryl-carbonyl.

Preferred compounds are those in which at least one, and more preferably both of R$_1$ and R$_2$ are hydrogen or lower alkyl.

Compounds in accordance with the present invention are readily prepared employing known starting materials and procedures. It will be understood by those skilled in the art that the carbon atoms to which R$_1$ and

are attached can be asymmetric centers, such that the inventive compounds may exist in (R,R), (R,S), (S,R), and (S,S) forms. The carbon atom to which R$_2$ is attached can also be an asymmetric center. Individual isomers and diastereo-isomeric mixtures of said forms are within the scope of the invention. The preferred forms have (S,S) or (S,S,S) configuration.

The compounds of the formula (1) can be prepared by reacting a compound of the formula (2):

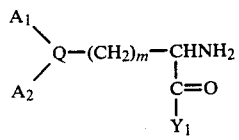

with compound (3):

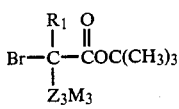

wherein $A_1$, $A_2$, m, $Y_1$, $R_1$, $Z_3$ and $M_3$ are as defined hereinabove, except that $Y_1$ is preferably ethoxy to protect against unwanted bond formation at the $Y_1$ site. The product of reacting compounds (2) and (3), which is compound (4),

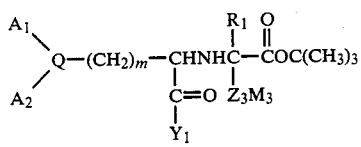

is reacted with 2,2,2-trichloroethyl chloroformate to protect the nitrogen atom, and the N-protected product is reacted with strong HCl to remove the t-butyl esterifying group to form compound (5):

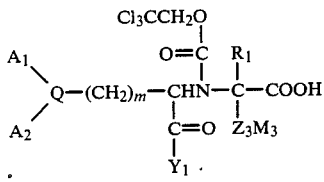

Compound (5) is reacted with compound (6):

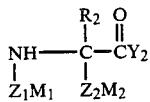

The reaction can be carried out by converting compound (5) to the acid chloride by reaction with oxalyl chloride, and then adding compound (6). Alternatively, compounds (4) and (6) can be condensed directly, following hydrolysis of the t-butyl ester to the acid, in the presence of a suitable coupling agent such as DCC (dicyclohexylcarbodiimide) or CDI (N,N'-carbonyldiimidazole) in a reaction familiar to those of ordinary skill in the peptide synthesis art. While proceeding via a coupling agent is preferred when the reaction can be made to proceed with a yield higher than that provided by the corresponding acid chloride route, this route's likelihood of success is often determined on a case-by-case basis; thus, in an overall sense the acid chloride route is preferred except where the direct-coupling route is found to work better.

Compound (6) can be prepared by procedures within the skill of the art. For instance, the amino acid

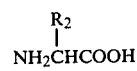

can be N-protected with a carbonylbenzyloxy or similar protecting group, then substituted with the desired $Z_2M_2$ at the alpha-carbon. The nitrogen is then de-protected and substituted with the desired $Z_1M_1$ group, and the resultant compound is reacted with compound (5) to give compound (7):

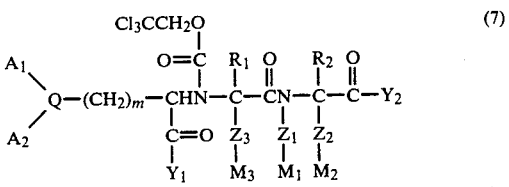

Compound (7) is de-N-protected with zinc in acetic acid, and then, if desired, ester groups such as in the $Y_1$ and/or $Y_2$ position are converted to the free acid with commonly known reagents such as HCl or NaOH. As can be seen in the accompanying Examples, methods are known for converting some but not all of the esterified groups to the acid. Each of the above reactions proceeds in a straightforward manner in a suitable solvent at temperatures ranging from 0° C. to 150° C.

The reaction products are sometimes obtained as a mixture of diasteroisomers which can be separated by standard methods of fractional crystallization or chromatography.

The compounds of this invention form acid salts with various inorganic and organic acids which are also within the scope of the invention. The pharmaceutically-acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically-acceptable acid salts are the salts of hydrochloric, hydrobromic, sulfuric, nitric, acetic, fumaric, malic, maleic and citric acids.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin-to-angiotensin I-to-angiotensin II sequence inhibit angiotensin I converting enzyme and therefore are useful in reducing or relieving hypertension. Furthermore, the compounds within the scope of the present invention which possess diuretic activity promote relief from hypertension by promoting diuresis, and consequently have utility in treating congestive heart failure. Compounds within the scope of the present invention can also simultaneously possess ACE inhibitory and diuretic activity, which is particularly unexpected in view of the fact that such simultaneous activity cannot be predicted from prior art compounds. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as pepermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, mthyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE 1

A mixture of 25.3 gm (0.141 mol) of L-2-amino-4-phenylbutyric acid (I-A) in 400 ml of 5N ethanolic hydrogen chloride was stirred at room temperature for 7 days. The reaction mixture was concentrated in vacuo and the product triturated with ether. The white solid was filtered off, dissolved in a saturated solution of aqueous potassium carbonate, and extracted twice with ethyl acetate. The organic portions were combined, washed once with brine, dried over magnesium sulfate, filtered, and concentrated in vacuo to give 23.6 gm (81%) of ethyl L-2-amino-4-phenylbutyrate (I-B) as an oil: $[\alpha]_D^{MeOH} = +35.5°$.

A mixture containing 96.2 gm (0.629 mol) of 2-bromopropionic acid, 64.0 gm (0.592 mol) of benzyl alcohol, and 2 ml of concentrated sulfuric acid in 200 ml of methylene chloride was refluxed for 22 hours. The reaction mixture was cooled to room temperature and washed successively with water, saturated aqueous potassium carbonate, saturated aqueous sodium bicarbonate, and water. It was then dried over magnesium sulfate, filtered, concentrated in vacuo and distilled via short path to give a fraction (bp 90°–110° C.; 0.1 mm Hg) containing 62.1 gm (43%) of benzyl 2-bromopropionate (I-C) as an oil.

A mixture of 9.6 gm (0.046 mol) of compound (I-B), 17.0 gm (0.069 mol) of compound (I-C), and 7.0 ml (0.050 mol) of triethylamine in 100 ml of acetonitrile was refluxed for 12 hours. The reaction mixture was filtered and concentrated in vacuo. The residue was taken up in ether and washed with a saturated aqueous solution of sodium bicarbonate and with brine. It was dried over magnesium sulfate, filtered, concentrated in vacuo, and the residue chromatographed via HPLC [Water's 500, 10% ethyl acetate in hexanes] to give N-[(1S)-1-ethoxycarbonyl-3-phenylpropyl]-D-alanine benzyl ester followed by 4.6 gm (27%) of N-[(1S)-1-ethoxycarbonyl-3-phenylpropyl]-L-alanine benzyl ester (I-D) as oils.

A mixture of 5.40 gm (14.6 mmol) of compound (I-D) and 1.0 gm of 10% palladium on activated carbon in 300 ml of absolute ethanol was hydrogenated at 40 psi for 2 hours. The mixture was filtered and the filtrate concentrated in vacuo. The residue was triturated with pentane and filtered to give 3.25 gm (80%) of N-[(1S)-1-ethoxycarbonyl-3-phenylpropyl]-L-alanine (I-E) as a white solid: mp 147°–148° C.

To a vigorously stirred solution of 50 ml (1.58 mol) of anhydrous hydrazine in 5 liters of ether at room temperature was added portionwise 32.5 gm (0.128 mol) of 4-chloro-3-sulfamoylbenzoyl chloride. After 2 hours the mixture was allowed to settle and the supernatant was decanted. The residue was then dissolved in 300 ml of hot water. The hot solution was filtered and the filtrate cooled overnight. The precipitate was filtered off, washed with ether, and dried in vacuo to give 10.2 gm (32%) of 4-chloro-3-sulfamoylbenzoyl hydrazide (I-F) as a white crystalline solid: mp 228°–231° C.

To a stirred suspension containing 14.5 gm (58.1 mmol) of compound (I-F) and 8.04 gm (58.2 mmol) of potassium carbonate in 60 ml of N,N-dimethylformamide at 0° C. was added dropwise over 1 hour 9.59 ml (59.4 mmol) of t-butyl bromoacetate. After stirring for 1 hour at room temperature the reaction mixture was poured into 500 ml of water and extracted three times with ethyl acetate. The combined organic portions were dried over magnesium sulfate, filtered, and concentrated in vacuo. The product was chromatographed via HPLC [Water's 500, 72% ethyl acetate in hexanes, k'=5.5] to afford a solid product, which upon recrystallization from ethyl acetate/hexanes gave 5.75 gm (27%) of 1-t-butylcarboxymethyl-2-(4-chloro-3-sulfamoylbenzoyl)hydrazine (I-G) as a white crystalline solid: mp 125°–128° C.

To a solution containing 0.84 gm (3.0 mmol) of compound (I-E), 1.09 gms (2.98 mmol) of compound (I-G), and 0.811 gm (5.29 mmol) of 1-hydroxybenzotriazole hydrate in 25 ml of dry tetrahydrofuran at 0° C. and under an atmosphere of nitrogen was added dropwise a solution of 0.62 gm (3.0 mmol) of N,N'-dicyclohexylcarbodiimide in 10 ml of dry tetrahydrofuran. The reaction mixture was then allowed to gradually warm to room temperature. After 1.5 hours 0.40 ml (2.9 mmol) of triethylamine was added dropwise to the solution. The mixture was then allowed to stir overnight, after which it was filtered and concentrated in vacuo. The residue was taken up in ethyl acetate and washed twice with a saturated aqueous solution of sodium bicarbonate and once each with water and brine. The organic phase was dried over magnesium sulfate, filtered, and concentrated in vacuo. The product was chromatographed via HPLC [Water's 500, 35% methylene chloride in ether, k'=4.9] to yield 424 mg (23%) of 1-[N-[(1S)-1-ethoxycarbonyl-3-phenylpropyl]-L-alanyl]-1-t-butylcarboxymethyl-2-(4-chloro-3-sulfamoylbenzoyl)hydrazine (I-H) as a glass.

A mixture containing 420 mg (0.672 mmol) of compound (I-H) in 15 ml of 4N hydrogen chloride in dioxane was stirred for 15.5 hours at room temperature. The mixture was concentrated in vacuo and the residue triturated with ether and filtered to give 408 mg (100%) of 1-[N-[(1S)-1-ethoxycarbonyl-3-phenylpropyl]-L-alanyl]-1-carboxymethyl-2-(4-chloro-3-sulfamoylbenzoyl)hydrazine hydrochloride (I-I) as a white solid: mp 144° C. (softens).

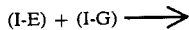

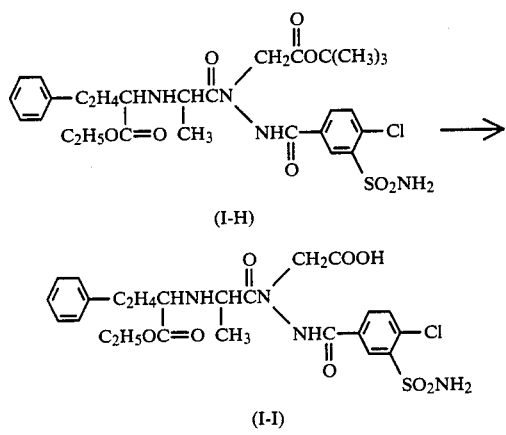

EXAMPLE II

To a mixture of 122.6 gm (0.801 mol) of 2-bromo propionic acid and 2.5 ml of concentrated sulfuric acid in 400 ml of methylene chloride at −78° C. and under an atmosphere of nitrogen was bubbled 300 ml of isobutylene. The reaction mixture was slowly allowed to warm to room temperature. After 22 hours the mixture was concentrated in vacuo and the residue taken up in ether and washed three times with a saturated aqueous solution of sodium carbonate and once with brine. It was dried over magnesium sulfate, filtered, and concentrated in vacuo to yield 104.9 gm (63%) of t-butyl 2-bromopropionate (II-A) as an oil.

A mixture of 24.0 gm (0.116 mol) of compound (I-B), 31.1 gms (0.148 mol) of compound (II-A), and 18.0 ml (0.129 mol) of triethylamine in 200 ml of acetonitrile was refluxed for 10 hours. The reaction mixture was filtered and concentrated in vacuo. The residue was taken up in ether and washed twice with water, once with a saturated aqueous solution of potassium carbonate, once with water again, and once with brine. It was dried over magnesium sulfate, filtered, concentrated in vacuo, and chromatographed via HPLC [Water's 500, 10% ethyl acetate in hexanes] to give 11.83 gms (31%) of N-[(1S)-1-ethoxycarbonyl-3-phenylpropyl]-D-alanine t-butyl ester (k'=2.6) and 15.75 gm (41%) of N-[(1S)-1-ethoxycarbonyl-3-phenylpropyl]-L-alanine t-butyl ester (II-B) (k'=4.0).

A mixture of 10.00 gm (29.81 mmol) of compound (II-B), 4.00 ml (49.5 mmol) of pyridine and 4.40 ml (32.0 mmol) of 2,2,2-trichloroethyl chloroformate in 75 ml of dry tetrahydrofuran under an atmosphere of nitrogen was refluxed for 3.5 hours. The reaction mixture was filtered and concentrated in vacuo. The residue was taken up in ether and washed four times with 1N aqueous hydrochloric acid and once with brine. The organic phase was dried over magnesium sulfate, filtered, and concentrated in vacuo. The product was chromatographed via HPLC [Water's 500, 15% ether in hexanes, k'=2.4] to afford 13.78 gm (90%) of N-[(1S)-1-ethoxycarbonyl-3-phenylpropyl]-N-(2,2,2-trichloroethoxycarbonyl)-L-alanine t-butyl ester (II-C) as an oil.

A mixture containing 13.72 gm (26.86 mmol) of compound (II-C) in 150 ml of 4N hydrogen chloride in dioxane under an atmosphere of nitrogen was stirred for 9 hours at room temperature. The mixture was concentrated in vacuo and the residue chromatographed on silica gel [20 cm×5.2 cm, hexanes 70% ether in hexanes] to afford 10.22 gm (84%) of N-[(1S)-1-ethoxycarbonyl-3-phenylpropyl]-N-(2,2,2-trichloroethoxy-carbonyl)-L-alanine (II-D) which solidified on standing: mp 73°–75° C.

A mixture of 46.8 gm (0.173 mol) of 2,4-dichloro-5-sulfamoylbenzoic acid in 400 ml of 5N ethanolic hydrogen chloride solution was stirred at room temperature for 64 hours. The reaction mixture was concentrated in vacuo and the product recrystallized from hot ether to yield 38.5 gms (75%) of ethyl 2,4-dichloro-5-sulfamoylbenzoate (II-E): mp 119°–122° C.

A mixture containing 29.9 gm (0.017 mol) of Nα-benzyloxycarbonyl-L-lysine, 30 ml of ethanol, and 9.0 ml of concentrated sulfuric acid in 250 ml of methylene chloride was refluxed for 22.5 hours. The reaction mixture was then cooled to room temperature and basified to pH of about 13 by the careful addition of a saturated aqueous solution of potassium carbonate. The aqueous phase was removed and the organic phase was washed one more time with a saturated potassium carbonate solution. The organic phase was dried over magnesium sulfate, filtered and concentrated in vacuo to give 29.8 gm (91%) of ethyl Nα-benzyloxycarbonyl-L-lysinate (II-F) as an oil.

A mixture containing 20.6 gm (66.8 mmol) of compound (II-F) and 8.50 gm (28.5 mmol) of compound (II-E) in 30 ml of tetrahydrofuran was refluxed for 51 hours. The reaction mixture was concentrated in vacuo to give a residue which was taken up in ethyl acetate and washed once with 10% aqueous acetic acid and once with water. The organic portion was dried over magnesium sulfate, filtered and concentrated in vacuo to give a viscous oil which was chromatographed via HPLC [Water's 500, 80% ether in hexanes, k'=6.0] to give 9.6 gm (59%) of a mixture of the wo regioisomers: ethyl Nα-benzyloxycarbonyl-Nε-(5-chloro-2-ethoxycarbonyl-4-sulfamoylphenyl)-L-lysinate (II-Ga) (mp 86°–89° C.) and ethyl Nα-benzyloxycarbonyl-Nε-(5-chloro-4-ethoxycarbonyl-2-sulfamoylphenyl)-L-lysinate (II-Gb) (mp 140°–143° C.).

A mixture containing 10.2 gm (17.9 mmol) of a mixture of compounds (II-Ga) and (II-Gb) in 200 ml of 1.8M hydrogen bromide in glacial acetic acid was stirred at room temperature for 4.25 hours. The reaction mixture was diluted with 3.0 liters of ether and the precipitated product was collected and triturated with ether. The solidified product was filtered from the suspension to give 7.73 gm (84%) of a mixture of regioisomers: ethyl Nε-(5-chloro-2-ethoxycarbonyl-4-sulfamoylphenyl)-L-lysinate hydrobromide (II-Ha) and ethyl Nε-(5-chloro-4-ethoxycarbonyl-2-sulfamoylphenyl)-L-lysinate hydrobromide (II-Hb).

To a mixture containing 7.73 gm (15.0 mmol) of compounds (II-Ha) and (II-Hb) and 4.20 ml (30.1 mmol) of triethylamine in 100 ml of dry tetrahydrofuran at room temperature was added dropwise 2.00 ml (16.8 mmol) of benzyl bromide. The mixture was then refluxed for 7.5 hours after which it was filtered and concentrated in vacuo. The residue was chromatographed via HPLC [Water's 500, 15% ether in methylene chloride] to give separately 1.5 gm (19%) of ethyl Nα-benzyl-Nε-(5-chloro-2-ethoxycarbonyl-4-sulfamoylphenyl)-L-lysinate (II-I) (k'=3.3) and 1.5 gm (19%) of ethyl Nα-benzyl-Nε-(5-chloro-4-ethoxycarbonyl-2-sulfamoylphenyl)-L-lysinate (II-J) (k'=7.4).

To a mixture containing 728 mg (1.60 mmol) of compound (II-D) in 10 ml of dry methylene chloride at room temperature and under an atmosphere of nitrogen was added dropwise 0.40 ml (4.59 mmol) of oxalyl chloride followed by 10 μL (0.13 mmol) of N,N-dimethylformamide. The object of this step was to convert compound (II-D) to its acid chloride. After 3.5 hours the reaction mixture was concentrated in vacuo and the resultant acid chloride was dissolved in 3 ml of dry methylene chloride. To this mixture was then added dropwise a solution containing 820 mg (1.56 mmol) of compound (II-I) and 0.250 ml (1.79 mmol) of triethylamine in 6 ml of dry methylene chloride. After 1 hour the reaction mixture was taken up in methylene chloride and washed three times with 1N aqueous hydrochloric acid, once with a saturated aqueous solution of sodium bicarbonate, and once with brine. The organic portion was dried over magnesium sulfate, filtered, and concentrated in vacuo to give crude ethyl Nα-benzyl-Nα-[N-[(1S)-1-ethoxycarbonyl-3-phenylpropyl]-N-(2,2,2-trichloroethoxycarbonyl)-L-alanyl]-Nε-(5-chloro-2-ethoxycarbonyl-4-sulfamoylphenyl)-L-lysinate, which was utilized directly in the next step without further purification. The crude product dissolved in 10 ml of glacial acetic acid and under an atmosphere of nitrogen was treated with 1.20 gms (18.4 mmol) of zinc dust. After 1.75 hours the suspension was filtered through celite and concentrated in vacuo. The residue was taken up in methylene chloride and washed three times with a saturated aqueous solution of sodium bicarbonate and once with brine. The organic portion was dried over magnesium sulfate, filtered, and concentrated in vacuo. The product was chromatographed via HPLC [Water's 500, 55% ethyl acetate in hexanes, k'=4.5] to give 509 mg (41%) of ethyl Nα-benzyl-Nα-[N-[(1S)-1-ethoxycarbonyl-3-phenylpropyl]-L-alanyl]-Nε-(5-chloro-2-ethoxycarbonyl-4-sulfamoylphenyl)-L-lysinate (II-Kb). Treatment of this compound with etheral hydrogen chloride afforded 443 mg of its hydrochloride salt (II-K) as a white solid: mp 103°–107° C. (softens).

A mixture of 326 mg (0.396 mmol) of compound (II-K) and 3.0 ml of 1.0N (3.0 mmol) aqueous sodium hydroxide in 3 ml of ethanol was stirred at room temperature for 22 hours. The reaction mixture was acidified to pH 1 with 1.0N aqueous hydrochloric acid and then extracted four times with ethyl acetate. The organic portions were combined, washed once with brine, dried over magnesium sulfate, filtered, and concentrated in vacuo. The residue was triturated with ether and filtered to give 291 mg (99%) of Nα-benzyl-Nα-[N-[(1S)-1-carboxy-3-phenylpropyl]-L-alanyl]-Nε-(2-carboxy-5-chloro-4-sulfamoylphenyl)-L-lysine hydrochloride (II-L) as a white solid: mp 172°–176° C. (softens).

The reaction sequence was as follows:

(II-I) + (II-D) ⟶

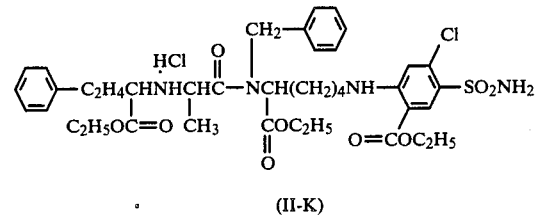

(II-K)

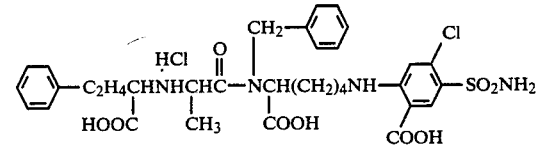

(II-L)

EXAMPLE III

Compound (II-D) and compound (II-J) were reacted with the identical sequence of reaction and isolation steps, and using the identical conditions and reagents, as were used to produce compound (II-K). The product, compound (III-A), was the hydrochloride salt of ethyl Nα-benzyl-Nα-[N-[(1S)-1-ethoxycarbonyl-3-phenylpropyl]-L-alanyl]-Nε-(5-chloro-4-ethoxycarbonyl-2-sulfamoylphenyl)-L-lysinate, a white solid mp 102°–106° C. (softens).

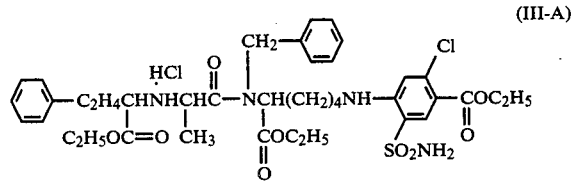

(III-A)

Compound (III-A) was reacted with sodium hydroxide and then hydrochloric acid, under the identical conditions to which compound (II-K) was subjected, to produce compound (III-B), Nα-benzyl-Nα-[N-[(1S)-1-carboxy-3-phenylpropyl]-L-alanyl]-Nε-(4-carboxy-5-chloro-2-sulfamoylphenyl)-L-lysine hydrochloride, a white solid mp 163°–165° C. (softens).

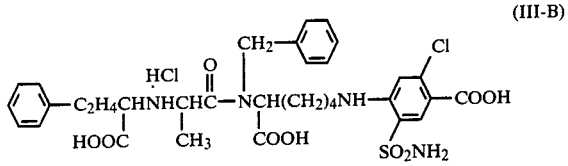

(III-B)

EXAMPLE IV

Into two separate 500 ml hydrogenation vessels each containing 100 ml of dioxane and 9.0 ml (160 mmol) of concentrated sulfuric acid was placed 11.0 gm (39.2 mmol) and 10.6 gm (37.8 mmol) of Nε-benzyloxycarbonyl-L-lysine. The two solutions were cooled to −78° C. and 140 ml of condensed (−78° C.) isobutylene was added to each vessel. The mixtures were then mechanically shaken (Parr shaker) at room temperature for 4 hours (26 psi). The reaction mixtures were combined and poured into 1000 ml (1.0 mol) of an ice cold solution of 1.0N aqueous sodium hydroxide and subsequently extracted three times with ether. The organic portions were combined (ca. 3000 ml), washed once with brine, dried over magnesium sulfate, filtered and concentrated in vacuo to give 16.7 gm (64%) of t-butyl Nε-benzyloxycarbonyl-L-lysinate (IV-A) as an oil.

To a solution containing 20.1 gms (59.7 mmol) of compound (IV-A) and 4.80 ml (59.3 mmol) of pyridine in 150 ml of dry tetrahydrofuran at −5° C. and under an atmosphere of nitrogen was added dropwise over a 15 minute period 8.50 ml (60.2 mmol) of trifluoroacetic anhydride. The reaction mixture was slowly allowed to warm to room temperature. After 16 hours the mixture was concentrated in vacuo. The residue was taken up in ether and washed twice with 1.0N aqueous hydrochloric acid, twice with a saturated aqueous solution of sodium bicarbonate, and once with brine. The organic portion was dried over magnesium sulfate, filtered, and concentrated in vacuo to afford a solid which was recrystallized from ether/hexanes to give 20.1 gm (78%) of t-butyl Nε-benzyloxycarbonyl-Nα-trifluoroacetyl-L-lysinate (IV-B): mp 77°–79° C.

A mixture of 24.7 gm (57.1 mmol) of compound (IV-B) and 2.87 gm of 10% palladium on activated carbon in 250 ml of absolute ethanol was hydrogenated at 55 psi for 2 hours. The mixture was filtered through celite and the filtrate concentrated in vacuo to give 17.0 gm (100%) of t-butyl Nα-trifluoroacetyl-L-lysinate (IV-C) as a viscous oil.

To a mixture containing 17.7 gm (59.3 mmol) of compound (IV-C) and 18.0 ml (129 mmol) of triethylamine in 100 ml of dry tetrahydrofuran at −5° C. and under an atmosphere of nitrogen was added dropwise over a 30 minute period a solution of 15.4 gm (60.7 mmol) of 4-chloro-3-sulfamoylbenzoyl chloride in 70 ml of dry tetrahydrofuran. The solution was slowly allowed to warm to room temperature. After 64 hours the mixture was concentrated in vacuo. The residue was taken up in ethyl acetate and washed twice with 1.0N aqueous hydrochloric acid, twice with a saturated aqueous solution of sodium bicarbonate, and once with brine. The organic portion was dried over magnesium sulfate, filtered, and concentrated in vacuo to afford an oil which was chromatographed via HPLC [Water's 500, 50% ethyl acetate in hexanes, k'=3.0] to yield 16.8 gm (55%) of t-butyl Nε-(4-chloro-3-sulfamoylbenzoyl)-Nα-trifluoroacetyl-L-lysinate (IV-D) as a glass.

A mixture containing 11.10 gm (21.51 mmol) of compound (IV-D) and 53.0 ml (53.0 mmol) of 1.0N aqueous sodium hydroxide in 50 ml of ethanol was stirred at room temperature for 5 hours. The reaction was quenched by the addition of 80 ml (80.0 mmol) of 1.0N aqueous hydrochloric acid. The mixture was brought to pH=9 by the careful addition of a saturated aqueous solution of sodium bicarbonate and then was extracted three times with ethyl acetate. The organic portions were combined (ca. 500 ml), washed once with brine, dried over magnesium sulfate, filtered, and concentrated in vacuo. The product was recrystallized from ethyl acetate/hexanes to yield 6.74 gm (75%) of t-butyl Nε-(4-chloro-3-sulfamoylbenzoyl)-L-lysinate (IV-E) as a white solid: mp 158°–160° C.

A mixture containing 8.38 gm (19.1 mmol) of compound (IV-E), 34.1 gm (173 mmol) of 2-bromoindane, and 13.3 gm (158 mmol) of sodium bicarbonate in 130 ml of acetonitrile under an atmosphere of nitrogen was refluxed for 48 hours. The reaction mixture was concentrated in vacuo and the residue taken up in ethyl acetate and washed twice with water and once with brine. It was dried over magnesium sulfate, filtered, and concentrated in vacuo. The residue was chromatographed via HPLC [Water's 500, 70% ethyl acetate in hexanes, k'=3.8] to give 8.39 gm (82%) of t-butyl Nε-(4-chloro-3-sulfamoylbenzoyl)-Nα-(2,3-dihydro-1H-inden-2-yl)-L-lysinate (IV-F): mp 65°–68° C.; [α]$_D^{MeOH}$ = +14.7°.

To a mixture containing 4.64 gm (10.2 mmol) of product (II-D) in 40 ml of dry methylene chloride at room temperature and under an atmosphere of nitrogen was added dropwise 7.30 ml (83.8 mmol) of oxalyl chloride followed by 30 μL (0.39 mmol) of N,N-dimethylformamide. After 3.5 hours the reaction mixture was concentrated in vacuo. The residue (ca. 4.9 gm) was dissolved in 25 ml of dry methylene chloride, placed under an atmosphere of nitrogen, and cooled to −5° C. To this mixture was then added dropwise over a 25 minute period a solution of 3.98 gm (7.42 mmol) of compound (IV-F) and 7.50 ml (53.8 mmol) of triethylamine in 40 ml of dry methylene chloride. The solution was slowly allowed to warm to room temperature. After 15.25 hours the reaction mixture was concentrated in vacuo. The residue was taken up in ethyl acetate and washed four times with 1.0N aqueous hydrochloric acid (ca. 1000 ml) and once with brine. It was dried over magnesium sulfate, filtered, and concentrated in vacuo. The product was chromatographed via HPLC [Water's 500, 7% acetic acid in ethyl acetate, k'=5.8] to give 5.02 gm (70%) of t-butyl Nε-(4-chloro-3-sulfamoylbenzoyl)-Nα-(2,3-dihydro-1H-inden-2-yl)-Nα-[N-[(1S)-1-ethoxycarbonyl-3-phenylpropyl]-N-(2,2,2-trichloroethoxycarbonyl)-L-alanyl]-L-lysinate (IV-G) as a glass.

A mixture of 5.02 gm (5.16 mmol) of compound (IV-G) in 25 ml of glacial acetic acid at room temperature and under an atmosphere of nitrogen was treated with 9.80 gm (150 mmol) of zinc dust. After 7 hours the suspension was filtered through celite and the filtrate was concentrated in vacuo. Trituration of the residue with ether afforded 4.71 gm of a solid which was dissolved in a saturated aqueous solution of sodium bicarbonate. The solution was then extracted three times with ethyl acetate. The organic portions were combined, washed once with brine, dried over magnesium sulfate, filtered, and concentrated in vacuo. The product was chromatographed via HPLC [Water's 500, ethyl acetate/hexanes/methanol (5/4/1), k'=2.7] to afford t-butyl Nε-(4-chloro-3-sulfamoylbenzoyl)-Nα-

(2,3-dihydro-1H-inden-2-yl)-Nα-[N-[(1S)-1-ethoxycarbonyl-3-phenylpropyl]-L-alanyl]-L-lysinate. Treatment of this compound with etheral hydrogen chloride yielded 2.88 gm (67%) of its hydrochloride salt (IV-H) as a white solid.

A mixture containing 1.14 gm (1.36 mmol) of compound (IV-H) in 50 ml of 4N hydrogen chloride in dioxane at room temperature and under an atmosphere of nitrogen was stirred for 17 hours. The mixture was concentrated in vacuo and the residue was triturated with hexanes, filtered off and dried (T about 70° C.) under vacuum to give 844 mg (80%) of Nε-(4-chloro-3-sulfamoylbenzoyl)-Nα-(2,3-dihydro-1H-inden-2-yl)-Nα-[N-[(1S)-1-ethoxycarbonyl-3-phenylpropyl]-L-alanyl]-L-lysine hydrochloride (IV-I) as a white solid: mp 158°–162° C. (softens).

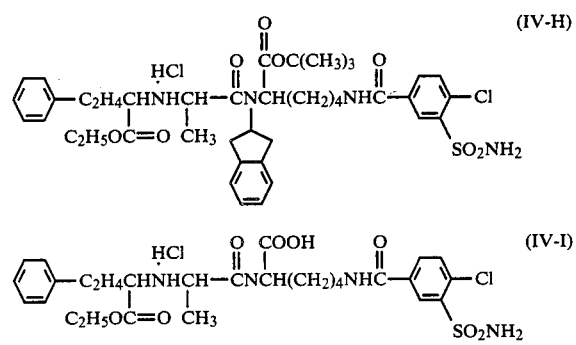

EXAMPLE V

A solution of sodium bisulfite (72.8 g, 0.70 m) in water (390 ml) was added dropwise to a boiling mixture of 4-chloro-3-nitro-5-sulfamylbenzoic acid (38.6 g, 0.14 m) in water (390 ml). The mixture was then refluxed 1 hour, acidified to pH 2 with concentrated hydrochloric acid, and refluxed another 30 minutes. On cooling a white precipitate formed which was collected and washed with water. Yield: 23.9 g (68%) of 3-amino-4-chloro-5-sulfamoylbenzoic acid (V-A).

Compound (V-A) (10.0 g, 0.040 m) was dissolved in ethanol (100 ml)/sulfuric acid (1.5 ml) and refluxed for 5 hours. The solution was concentrated in vacuo and the residue treated with saturated sodium bicarbonate solution. The resulting solid was collected, washed with water and recrystallized from aqueous ethanol. Yield: 6.8 g (61%) of ethyl 3-amino-4-chloro-5-sulfamoyl benzoate (V-B).

Disodium iminodiacetate monohydrate (11.7 g, 0.060 m) was dissolved in water (40 ml) and cooled to 0°. Benzyl chloroformate (13.3 g, 0.078 m) was added in portions as the pH of the solution was kept at 9–12 by addition of 2N sodium hydroxide solution as needed. When addition was complete the mixture was stirred an additional 3 hours at 0°–10° C., then extracted with diethyl ether. The aqueous layer was acidified with concentrated hydrochloric acid and extracted with ethyl acetate. The organic layer was separated, dried over sodium sulfate and concentrated to give 13.0 g (81%) of N-benzyloxycarbonyliminodiacetic acid (V-C).

Compound (V-C) (6.3 g, 24 mmol) and acetic anhydride (13.0 g, 0.127 m), were combined and stirred 2 days at room temperature. Acetic acid and anhydride were removed in vacuo and the residue was recrystallized from hexanes/ethyl acetate to give 7.2 g (78%) of N-benzyloxycarbonyliminodiacetic anhydride (V-D).

Compound (V-B) (5.6 g, 20 mmol) and compound (V-D) (5.5 g, 22 mmol) were dissolved in acetonitrile (80 ml) and stirred 3 days. The mixture was then filtered to give the desired product. Additional material of lower purity could be obtained by concentrating the filtrate and washing the brown residue with hexane/ethyl acetate. Total yield: 10.1 g (96%) of ethyl 3-[N-benzyloxycarbonyl-N-(carboxymethyl)-glycinamido]-4-chloro-5-sulfamoylbenzoate (V-E).

Compound (V-E) (10.1 g, 19.1 mmol) was combined with acetic acid containing 32% hydrogen bromide (60 ml total) and allowed to stand 1.75 hours. The slurry was then washed several times with ether and dried in vacuo at 80° to give ethyl 3-[N-(carboxymethyl)-glycinamido]-4-chloro-5-sulfamoylbenzoate hydrobromide (8.1 g, 89%). This material was dissolved in water (70 ml), the solution was filtered and neutralized with 1N sodium hydroxide solution (17 ml). The resulting precipitate was collected and washed with water and ethanol to give 6.1 g (91%) of ethyl 3-[N-(carboxymethyl)glycinamido]-4-chloro-5-sulfamoyl benzoate (V-F).

A solution of compound (V-F) (6.1 g, 15 mmol) in ethanol (125 ml) containing sulfuric acid (1 ml) was refluxed 24 hours and then concentrated in vacuo. Sodium bicarbonate solution was added and the precipitate was collected and washed with water. Yield: 5.7 g (87%) of ethyl 3-[N-(ethoxycarbonylmethyl)-glycinamido]-4-chloro-5-sulfamoyl benzoate (V-G).

A solution of compound (V-G) (2.97 g, 7.04 mmol) and triethylamine (0.819 g, 8.09 mmol) in dry tetrahydrofuran (100 ml) was added to a solution of 7.04 mmol of the acid chloride of compound (II-D) (see Example II) in 50 ml of tetrahydrofuran. After stirring overnight, the mixture was filtered and the filtrate was diluted with water until a second phase formed. The mixture was extracted with methylene chloride and the organic portion washed with 1N HCl, saturated sodium bicarbonate solution, and brine. After drying over sodium sulfate, the solution was concentrated in vacuo to provide 5.8 g (yield 96%) of a white foam, ethyl N-[N-[(1S)-1-ethoxycarbonyl-3-phenylpropyl]-N-(2,2,2-trichloroethoxycarbonyl)-L-alanyl]-N-[N-(2-chloro-5-ethoxycarbonyl-3-sulfamoylphenyl)-2-aminocarbonylmethyl]-glycinate (V-H).

Compound (V-H) (5.8 g, 6.7 mmol) was dissolved in acetic acid and zinc dust (5.9 g, 90 mmol) was added. The mixture was stirred vigorously for 4 hours, then filtered through celite. The filtrate was concentrated and residual acetic was azeotroped off with toluene. The residue was dissolved in ethyl acetate and the solution was washed with saturated sodium bicarbonate solution, water, and brine. The organic portion was dried over sodium sulfate and concentrated in vacuo to a foam, ethyl N-[N-[(1S)-1-ethoxycarbonyl-3-phenylpropyl]-L-alanyl]-N-[N-(2-chloro-5-ethoxycarbonyl-3-sulfamoylphenyl)-2-aminocarbonylmethyl]glycinate (V-I).

Sodium hydroxide (0.146 g, 3.65 mmol) in water (0.3 ml) was added to a solution of compound (V-I) (0.486 g, 0.71 mmol) in 3.0 ml of methanol. The solution was stirred two hours, then concentrated in vacuo at room temperature. The residue was dissolved in water and the solution was neutralized with concentrated HCl, whereupon a white precipitate formed. Filtration gave 0.24 g (yield: 56%) of N-[N-[(1S)-1-carboxy-3-phenylpropyl]-L-alanyl]-N-[N-(2-chloro-5-carboxy-3-sul-famoylphenyl)-2-aminocarbonylmethyl]glycine (V-J).

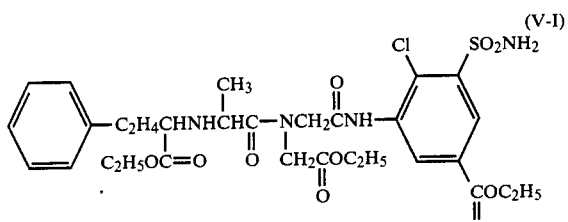

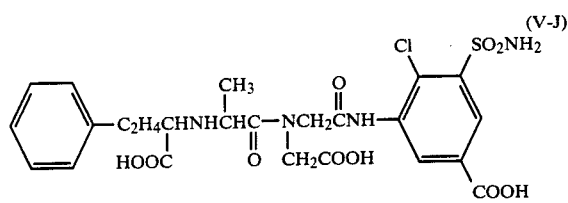

EXAMPLE VI

A mixture of 3-nitro-4-phenoxy-5-sulfamylbenzoic acid (3.7 g, 0.011 mol), 10% palladium on carbon (0.5 g) and ethanol (100 ml) was shaken on a Parr hydrogenator for 1.5 hours at a hydrogen pressure of 40 psi. The catalyst was filtered off and the filtrate was concentrated to a white solid. Yield: 3.2 g (94%) of 3-amino-4-phenoxy-5-sulfamoylbenzoic acid (VI-A).

A mixture of compound (VI-A) (6.17 g, 0.020 mmol), 2-nitroethyl acetate (2.66 g, 0.020 mmol), sodium acetate trihydrate (2.72 g, 0.020 mol), acetic acid (1.20 g, 0.020 mol) and water (6 ml) was heated to 75° over 20 minutes, then cooled. The precipitate was filtered and washed with water and ethanol to give 3.93 g (51.5%) of compound (VI-B), 3-(2-nitroethylamino)-4-phenoxy-5-sulfamoylbenzoic acid.

Compound (VI-B) (4.0 g, 10 mmol) and a catalytic amount of Raney Nickel were slurried in water (90 ml)/ethanol (90 ml). The mixture was hydrogenated on a Parr apparatus for 3.5 hours at an initial hydrogen pressure of 51 psi. The mixture was then filtered and the precipitate was extracted several times with hot water. The filtrate and extracts were combined and concentrated to yield 3.6 g (97%) of compound (VI-C), 3-(2-aminoethylamino)-4-phenoxy-5-sulfamoylbenzoic acid.

Compound (VI-C) (4.4 g, 12 mmol) was added to ethanol (150 ml), followed by sulfuric acid (1.5 ml). The solution was refluxed 18 hours, then concentrated in vacuo. The residue was dissolved in water and neutralized with sodium bicarbonate solution, then extracted with ethyl acetate. The organic layer was washed with brine, dried over sodium sulfate and concentrated to give 4.0 g (84%) of compound (VI-D), ethyl 3-(2-aminoethylamino)-4-phenoxy-5-sulfamoylbenzoate.

A mixture of bromoacetic acid (34.8 g, 0.25 mol), benzyl alcohol (27.0 g, 0.25 mol), p-toluenesulfonic acid (3 g, 0.02 mol) and cyclohexane (200 ml) was refluxed 6 hours in a flask equipped with a Dean Stark trap, condenser and mechanical stirrer. The mixture was cooled and stirred 10 minutes with saturated sodium bicarbonate solution (150 ml). The organic layer was then extracted four more times with saturated sodium bicarbonate solution, washed with water and brine, then concentrated in vacuo. The yield of benzyl bromoacetate was quantitative.

A solution of compound (VI-D) (2.8 g, 7.4 mmol) and triethylamine (1.0 g, 10 mmol) in tetrahydrofuran (100 ml) was cooled to 0°. Benzyl bromoacetate (1.9 g, 8.1 mmol) was added and the solution was allowed to stir at room temperature for 2 days. The mixture was filtered and the filtrate was concentrated in vacuo. The residue was purified by high-pressure liquid chromatography to provide compound (VI-E), ethyl 3-[2-[N-(benzyloxycarbonylmethyl)amino]-ethylamimo]-4-phenoxy-5-sulfamoyl benzoate. Proceeding via the t-butyl analog of this benzyl compound gives satisfactory results.

A solution of compound (VI-E) (0.93 g, 1.8 mmol) and triethylamine (0.20 g, 2.0 mmol) in tetrahydrofuran (25 ml) was added in one portion to 1.76 mmol of the acid chloride of compound (II-D) (see Example II) in tetrahydrofuran (10 ml). The mixture was stirred 2 hours and then filtered. The filtrate was diluted with an equal amount of water and the mixture was extracted with methylene chloride. The organic layer was separated, washed with water and brine, and dried over sodium sulfate. Concentration gave a foam (1.39 g, 82%) of compound (VI-F), benzyl N-[N-[(1S)-1-ethoxycarbonyl-3-phenylpropyl]-N-(2,2,2-trichloroethoxycarbonyl)-L-alanyl]-N-[N-(2-phenoxy-5-ethoxycarbonyl)-L-alanyl]-N-[N-(2-phenoxy-5-ethoxycarbonyl-3-sulfamoylphenyl)-2-aminoethyl]glycinate.

The —CO$_2$CH$_2$CCl$_3$ protecting group was removed from compound (VI-F) by dissolving 1.0 g (1.0 mmol) of compound (VI-F) in 6.9 ml of acetic acid and adding zinc dust (0.91 g, 14 mmol). The mixture was stirred 4 hours and filtered. The filtrate was concentrated in vacuo. The residue was purified by column chromatography to give compound (VI-G), benzyl N-[N-[(1S)-1-ethoxycarbonyl-3-phenylpropyl]-L-alanyl]-N-[N-(2-phenoxy-5-ethoxycarbonyl-3-sulfamoylphenyl)-2-aminoethyl]glycinate.

Compound (VI-G) is dissolved in ethanol and a catalytic amount of 10% palladium on carbon is added. The mixture is hydrogenated for 6 hours at an initial hydrogen pressure of 50 psi. The catalyst is filtered off and the filtrate concentrated to give the product (VI-H), N-[N-[(1S)-1-ethoxycarbonyl-3-phenylpropyl]-L-alanyl]-N-[N-(2-phenoxy-5-ethoxycarbonyl-3-sulfamoylphenyl)-2-aminoethyl]glycine.

Compound (VI-H) is added to an aqueous solution of sodium hydroxide in methanol. The mixture is stirred 2 hours, then concentrated in vacuo. The residue is dissolved in water and neutralized with concentrated hydrochloric acid. The resulting precipitate is collected, providing compound (VI-I), N-[N-[(1S)-1-carboxy-3-phenylpropyl]-L-alanyl]-N-[N-(2-phenoxy-5-carboxy-3-sulfamoylphenyl)-2-aminoethyl]glycine.

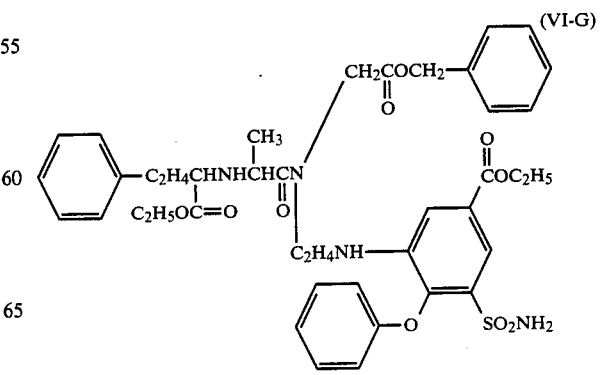

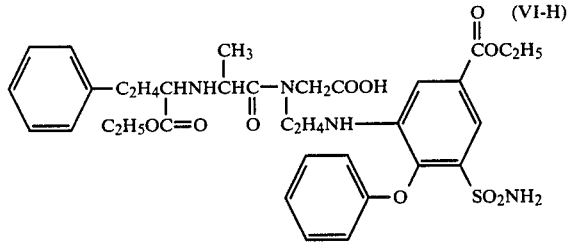

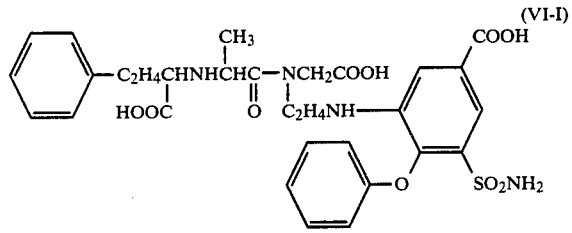

EXAMPLE VII

To a stirred solution of 50 ml (1.58 mol) of anhydrous hydrazine in 5 liters of ether at room temperature was added portionwise 32.5 gm (0.128 mol) of 4-chloro-3-sulfamoylbenzoyl chloride. After 2 hours the mixture was allowed to settle and the supernatant was decanted. The residue was then dissolved in 300 ml of hot water. The hot solution was filtered and the filtrate cooled overnight. The precipitate was filtered off, washed with ether, and dried in vacuo to give 10.2 gm (32%) of 4-chloro-3-sulfamoylbenzoyl hydrazide as a white crystalline solid: mp 228°–231° C.

To a stirred suspension containing 58.1 mmol of methylhydrazine and 8.04 gm (58.2 mmol) of potassium carbonate in 60 ml of N,N-dimethylformamide at 0° C. is added dropwise over 1 hour 9.59 ml (59.4 mmol) of t-butyl bromoacetate. After stirring for 1 hour at room temperature the reaction mixture is poured into 500 ml of water and extracted three times with ethyl acetate. The combined organic portions are dried over magnesium sulfate, filtered, and concentrated in vacuo. The product is chromatographed to afford N-(t-butylcarboxymethyl)-N'-methyl-hydrazine, which is reacted with an equimolar amount of 4-chloro-3-sulfamoylbenzoyl chloride to yield 1-t-butylcarboxymethyl-2-methyl-2-(4-chloro-3-sulfamoylbenzoyl)hydrazine (VII-B).

To a solution containing 0.84 gm (3.0 mmol) of N-[(1S)-1-ethoxycarbonyl-3-phenylpropyl]-L-alanine, 3.0 mmol of compound (VII-B), and 0.811 gm (5.29 mmol) of 1-hydroxybenzotriazole hydrate in 25 ml of dry tetrahydrofuran at 0° C. and under an atmosphere of nitrogen is added dropwise a solution of 0.62 gm (3.0 mmol) of N,N'-dicyclohexylcarbodiimide in 10 ml of dry tetrahydrofuran. The reaction mixture is then allowed to gradually warm to room temperature. After 1.5 hours 0.40 ml (2.9 mmol) of triethylamine is added dropwise to the solution. The mixture is then allowed to stir overnight, after which it is filtered and concentrated in vacuo. The residue is taken up in ethyl acetate and washed twice with a saturated aqueous solution of sodium bicarbonate and once each with water and brine. The organic phase is dried over magnesium sulfate, filtered, and concentrated in vacuo. The product is chromatographed to yield 1-[N-[(1S)-1-ethoxycarbonyl-3-phenylpropyl]-L-alanyl]-1-t-butylcarboxymethyl-2-(4-chloro-3-sulfamoylbenzoyl)-2-methylhydrazine (VII-C).

A mixture containing 0.672 mmol of compound (VII-C) in 15 ml of 4N hydrogen chloride in dioxane is stirred for 15.5 hours at room temperature. The mixture is concentrated in vacuo and the residue triturated with ether and filtered to give 1-[N-[(1S)-1-ethoxycarbonyl-3-phenylpropyl]-L-alanyl]-1-carboxymethyl-2-(4-chloro-3-sulfamoylbenzoyl]-2-methylhdyrazine hydrochloride.

EXAMPLE VIII

A solution of sodium bisulfite (72.8 g, 0.70 m) in water (390 ml) was added dropwise to a boiling mixture of 4-chloro-3-nitro-5-sulfamoylbenzoic acid (38.6 g, 0.14 m) in water (390ml). The mixture was then refluxed 1 hour, acidified to pH 2 with concentrated hydrochloric acid, and refluxed another 30 minutes. On cooling a white precipitate formed, 3-amino-4-chloro-5-sulfamoylbenzoic acid, which was collected and washed with water.

This compound was dissolved in ethanol (100 ml)/sulfuric acid (1.5 ml) and refluxed for 5 hours. The solution was concentrated in vacuo and the residue treated with saturated sodium bicarbonate solution. The resulting solid was collected, washed with water and recrystallized from aqueous ethanol, to yield ethyl 3-amino-4-chloro-5-sulfamoyl benzoate (VIII-A).

N-(1-Carboxyethyl)glycine disodium salt (0.060 m) is dissolved in water (40 ml) and cooled to 0°. Benzyl chloroformate (13.3 g, 0.078 m) is added in portions as the pH of the solution is kept at 9–12 by addition of 2N sodium hydroxide solution as needed. When addition is complete the mixture is stirred an additional 3 hous at 0°–10° C., then extracted with diethyl ether. The aqueous layer is acidified with concentrated hydrochloric acid and extracted with ethyl acetate. The organic layer is separated, dried over sodium sulfate and concentrated to give N-benzyloxycarbonyl-N-(1-carboxyethyl)glycine (VIII-B).

Compound (VIII-B) (20 mmol) and compound (V-B) (22 mmol) are dissolved in acetonitrile (80 ml) and stirred 3 days. The mixture is then filtered and chromatographed to give the desired product, ethyl 3-[N-benzyloxycarbonyl-N-(carboxymethyl)alaninamido]-4-chloro-5-sulfamoylbenzoate (VIII-C).

Compound (VIII-C) (19.1 mmol) is combined with acetic acid containing 32% hydrogen bromide (60 ml total) and allowed to stand for 2 hours. The slurry is then washed several times with ether and dried in vacuo at 80° C. to give ethyl 3-[N-(carboxymethyl)alaninamido]-4-chloro-5-sulfamoylbenzoate hydrobromide. This material is dissolved in water (70 ml), and the solution is filtered and neutralized with 1N sodium hydroxide solution (17 ml). The resulting precipitate is collected and washed with water and ethanol to give ethyl 3-[N-(carboxy-methyl)-alaninamido]-4-chloro-5-sulfamoyl benzoate (VIII-D).

A solution of compound (VIII-D) (15 mmol) in ethanol (125 ml) containing sulfuric acid (1 ml) is refluxed 24 hours and then concentrated in vacuo. Sodium bicarbonate solution is added and the precipitate is collected and washed with water. Yield: ethyl 3-[N-(ethoxycarbonylmethyl)alaninamido]-4-chloro-5-sulfamoyl benzoate (VIII-E).

A solution of compound (VIII-E) (7.04 mmol) and triethylamine (8.09 mmol) in dry tetrahydrofuran (100 ml) is added to a solution of 7.04 mmol of the acid chloride of N-[(1S)-1-ethoxycarbonyl-3-phenylpropyl]-N-(2,2,2-trichloroethoxycarbonyl)-L-alanine in 50 ml of tetrahydrofuran. After stirring overnight, the mixture is filtered and the filtrate is diluted with water until a second phase forms. The mixture is extracted with methylene chloride and the organic portion washed with 1N HCl, saturated sodium bicarbonate solution, and brine. After drying over sodium sulfate, the solution is concentrated in vacuo to provide [N-[N-[(1S)-1-ethoxycarbonyl-3-phenylpropyl]-N-(2,2,2-trichloroethoxycarbonyl)-L-alanyl]-N-(ethoxycarbonylmethyl)alanyl]-(2-chloro-5-ethoxycarbonyl-3-sulfamoyl)anilide (VIII-F).

Compound (VIII-F) (6.7 mmol) is dissolved in acetic acid and zinc dust (5.9 g, 90 mmol) is added. The mixture is stirred vigorously for 4 hours, then filtered through celite. The filtrate is concentrated and residual acetic acid is azeotroped off with toluene. The residue is dissolved in ethyl acetate and the solution washed with saturated sodium bicarbonate solution, water, and brine. The organic portion is dried over sodium sulfate and concentrated in vacuo to yield [N-[N-[(1S)-1-ethoxycarbonyl-3-phenylpropyl]-L-alanyl]-N-(ethoxycarbonylmethyl)-alanyl]-(2-chloro-5-ethoxycarbonyl-3-sulfamoyl)anilide (VIII-G).

Sodium hydroxide (0.146 g, 3.65 mmol) in water (0.3 ml) is added to a solution of compound (VIII-G) (0.71 mmol) in 3.0 ml of methanol. The solution is stirred two hours, then concentrated in vacuo at room temperature. The residue is dissolved in water and the solution is neutralized with concentrated HCl, to precipitate [N-[N-[(1S)-1-carboxy-3-phenylpropyl]-L-alanyl]-N-(carboxymethyl)-alanyl]-(2-chloro-5-carboxy-3-sulfamoyl)anilide (VIII-H).

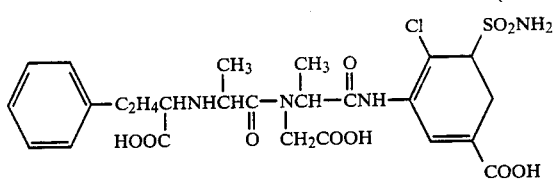

(VIII-H)

EXAMPLE IX

A mixture of 3-nitro-4-phenoxy-5-sulfamoylbenzoic acid (3.7 g, 0.011 mol), 10% palladium on carbon (0.5 g) and ethanol (100 ml) is shaken on a Parr hydrogenator for 1.5 hours at a hydrogen pressure of 40 psi. The catalyst is filtered off and the filtrate is concentrated to yield 3-amino-4-phenoxy-5-sulfamoylbenzoic acid (IX-A).

A mixture of compound (IX-A) (6.17 g, 0.020 mol), 2-nitrobutyl acetate (3.22 g, 0.020 mol), sodium acetate trihydrate (2.72 g, 0.020 mol), acetic acid (1.20 g, 0.020 mol) and water (6 ml) is heated to 75° over 20 minutes, then cooled. The precipitate is filtered and washed with water and ethanol to give compound (IX-B), 3-(2-nitrobutylamino)-4-phenoxy-5-sulfamoylbenzoic acid.

Compound (IX-B) (4.56 g, 10 mmol) and a catalytic amount of Raney Nickel are slurried in water (90 ml)/ethanol (90 ml). The mixture is hydrogenated on a Parr apparatus for 3.5 hours at an initial hydrogen pressure of 51 psi. The mixture is then filtered and the precipitate extracted several times with hot water. The filtrate and extracts are combined and concentrated to yield compound (IX-C), 3-(2-aminobutylamino)-4-phenoxy-5-sulfamoylbenzoic acid.

Compound (IX-C) (4.4 g, 12 mmol) is added to ethanol (150 ml), followed by sulfuric acid (1.5 ml). The solution is refluxed 18 hours, then concentrated in vacuo. The residue is dissolved in water and neutralized with sodium bicarbonate solution, then extracted with ethyl acetate. The organic layer is washed with brine, dried over sodium sulfate and concentrated to give compound (IX-D), ethyl 3-(2-aminobutylamino)-4-phenoxy-5-sulfamoylbenzoate.

A mixture of bromoacetic acid (34.8 g, 0.25 mol), benzyl alcohol (27.0 g, 0.25 mol), p-toluenesulfonic acid (3 g, 0.02 mol) and cyclohexane (200 ml) is refluxed 6 hours in a flask equipped with a Dean Stark trap, condenser and mechanical stirrer. The mixture is cooled and stirred 10 minutes with saturated sodium bicarbonate solution (150 ml). The organic layer is then extracted four more times with saturated sodium bicarbonate solution, washed with water and brine, then concentrated in vacuo. The yield of benzyl bromoacetate is quantitative.

A solution of compound (IX-D) (2.8 g, 7.4 mmol) and triethylamine (1.0 g, 10 mmol) in tetrahydrofuran (100 ml) is cooled to 0°. Benzyl bromoacetate (1.9 g, 8.1 mmol) is added and the solution is allowed to stir at room temperature for 2 days. The mixture is filtered and the filtrate is concentrated in vacuo. The residue is purified by high-pressure liquid chromatography to provide compound (IX-E), ethyl 3-[2-[N-(benzyloxycarbonylmethyl)amino]-butylamino]-4-phenoxy-5-sulfamoyl benzoate. Proceeding via the t-butyl analog of this benzyl compound gives satisfactory results.

A solution of compound (IX-E) (0.93 g, 1.8 mmol) and triethylamine (0.20 g, 2.0 mmol) in tetrahydrofuran (25 ml) is added in one portion to 1.76 mmol of the acid chloride of N-[(1S)-1-ethoxycarbonyl-3-phenylpropyl]-N-(2,2,2-trichloroethoxycarbonyl)-L-alanine in tetrahydrofuran (10 ml). The mixture is stirred 2 hours and then filtered. The filtrate is diluted with an equal amount of water and the mixture is extracted with methylene chloride. The organic layer is separated, washed with water and brine, and dried over sodium sulfate. Concentration gives compound (IX-F), benzyl N-[N-[(1S)-1-ethoxycarbonyl-3-phenylpropyl]-N-(2,2,2-trichloroethoxycarbonyl)-L-alanyl]-N-[[1-(N-(2-phenoxy-5-ethoxycarbonyl-3-sulfamoylphenyl)amino)methyl]propyl]-glycinate.

The —CO$_2$CH$_2$CCl$_3$ protecting group is removed from compound (IX-F) by dissolving 1.0 mmol of compound (IX-F) in 6.9 ml of acetic acid and adding zinc dust (0.91 g, 14 mmol). The mixture is stirred 4 hours and filtered. The filtrate is concentrated in vacuo. The residue is purified by column chromatography to give compound (IX-G), benzyl N-[N-[(1S)-1-ethoxycarbonyl-3-phenylpropyl]-L-alanyl]-N-[[1-(N-(2-phenoxy-5-ethoxycarbonyl-3-sulfamoylphenyl)amino)methyl]propyl]glycinate.

Compound (IX-G) is dissolved in ethanol and a catalytic amount of 10% palladium on carbon is added. The mixture is hydrogenated for 6 hours at an initial hydrogen pressure of 50 psi. The catalyst is filtered off and the filtrate concentrated to give the product (IX-H), N-[N-[(1S)-1-ethoxycarbonyl-3-phenylpropyl]-L-alanyl]-N-[[1-(N-(2-phenoxy-5-ethoxycarbonyl-3-sulfamoylphenyl)amino)methyl]propyl]glycine.

Compound (IX-H) is added to an aqueous solution of sodium hydroxide in methanol. The mixture is stirred 2 hours, then concentrated in vacuo. The residue is dissolved in water and neutralized with concentrated hydrochloric acid. The resulting precipitate is collected, providing compound (IX-I), N-[N-[(1S)-1-carboxy-3-phenylpropyl]-L-alanyl]-N-[[1-(N-(2-phenoxy-5-carboxy-3-sulfamoylphenyl)amino)methyl]propyl]glycine.

EXAMPLES X–XIX

The following compounds are made by procedures analogous to the aforementioned and within the skill of the art.

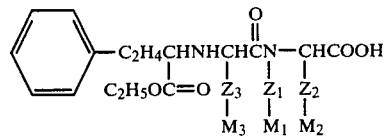

| EXAMPLE | COMPOUND |
|---|---|
| X | 1-[N—[(1S)—1-ethoxycarbonyl-3-phenyl-propyl]-L-alanyl]-1-carboxymethyl-2-(2-amino-4-chloro-5-sulfamoylbenzoyl) hydrazine |
| XI | 1-[N—[(1S)—1-ethoxycarbonyl-3-phenyl-propyl]-L-alanyl]-1-carboxymethyl-2-(2-chloro-3-sulfamoyl-5-ethoxycarbonylphenyl) hydrazine |
| XII | N—[N—[(1S)—1-ethoxycarbonyl-3-phenyl-propyl]L-alanyl]-N—[N—(2-chloro-3-sulfamoyl-5-ethoxycarbonylphenyl)-4-aminobutyl]glycine |
| XIII | 6-Chloro-3,4-dihydro-3-[N—(carboxy-methyl)-N—[N—[(1S)—1-ethoxycarbonyl-3-phenylpropyl]-L-alanyl]aminomethyl]-7-sulfamoyl-2H—1,2,4-benzothiadiazine-1,1-dioxide |
| XIV | Nε-(2-Amino-chloro-5-sulfamoyl-benzoyl)-Nα-benzyl-Nα-[N—[(1S)—1-ethoxycarbonyl-3-phenylpropyl]-L-alanyl]-L-lysine |
| XV | N—[Nα-[(1S)—1-ethoxycarbonyl-3-phenyl-propyl]-Nε-[2-amino-4-chloro-5-sulfamoylbenzoyl]-L-lysyl]-L-proline |
| XVI | 1-[N—[(1S)—1-ethoxycarbonyl-3-phenyl-propyl]-L-alanyl]-1-carboxymethyl-2-(2-amino-4-chloro-5-sulfamoylbenzoyl)2-methylhydrazine |
| XVII | 1-[N—[(1S)—1-ethoxycarbonyl-3-phenyl-propyl]-L-alanyl]-1-carboxymethyl-2-(2-chloro-3-sulfamoyl-5-ethoxycarbonylphenyl)-2-methylhydrazine |
| XVIII | N—[N—[(1S)—1-ethoxycarbonyl-3-phenyl-propyl]-L-alanyl]-N—[4-[N—(2-chloro-3-sulfamoyl-5-ethoxycarbonylphenyl)amino]-1-methylbutyl]glycine |
| XIX | N—[1-(5-t-butyl-2-hydroxyl-3-iodo-phenyl)-ethyl]-N—[N—[(1S)—1-ethoxy-carbonyl-3-phenyl-propyl]-L-alanyl]glycine |

| Example | —$Z_1M_1$ | —$Z_2M_2$ | —$Z_3M_3$ |
|---|---|---|---|
| X | —NHC(=O)—[phenyl with SO₂NH₂, Cl, NH₂] | —H | —CH₃ |
| XI | —NH—[phenyl with COC₂H₅(=O), Cl, SO₂NH₂] | —H | —CH₃ |
| XII | —(CH₂)₄NH—[phenyl with COC₂H₅(=O), Cl, SO₂NH₂] | —H | —CH₃ |

| Example | $-Z_1M_1$ | | $-Z_3M_3$ |
|---|---|---|---|
| XIII | −CH₂CH(NH−SO₂)(NH)−[benzene ring with Cl and SO₂NH₂] | −H | −CH₃ |
| XIV | −CH₂−C₆H₅ | −(CH₂)₄NHC(=O)−[benzene with SO₂NH₂, Cl, NH₂] | −CH₃ |

| | $-Z_1M_1-Z_2M_2-$ | |
|---|---|---|
| XV | −(CH₂)₃− | −(CH₂)₄NHC(=O)−[benzene with NH₂, Cl, SO₂NH₂] |

| Example | $-Z_1M_1$ | $-Z_2M_2$ | $-Z_3M_3$ |
|---|---|---|---|
| XVI | −N(CH₃)C(=O)−[benzene with SO₂NH₂, Cl, NH₂] | −H | −CH₃ |
| XVII | −N(CH₃)−[benzene with COC₂H₅, Cl, SO₂NH₂] | −H | −CH₃ |
| XVIII | −CH(CH₃)−(CH₂)₃NH−[benzene with COC₂H₅, Cl, SO₂NH₂] | −H | −CH₃ |
| XIX | −CH(CH₃)−[phenol with OH, I, C(CH₃)₃] | −H | −CH₃ |

EXAMPLES XX-XXX

The following compounds have been made following the procedures described herein and have been found to inhibit the activity of the angiotensin converting enzyme.

| | |
|---|---|
| XX | Nα-Benzyl-Nα-[N—[(1S)—1-ethoxycarbonyl-3-phenylpropyl]-L-alanyl]-Nε-(5-chloro-2-ethoxycarbonyl-4-sulfamoylphenyl)-L-lysine |
| XXI | N—(5-t-butyl-2-hydroxyl-3-iodobenzyl)-N—[N—[(1S)—1-ethoxycarbonyl-3-phenylpropyl]-L-alanyl]-glycine |

| | -continued |
|---|---|
| XXII | 6-Chloro-3,4-dihydro-3-[N—(ethoxy-carbonylmethyl)-N—[N'—[(1S)—1-ethoxy-carbonyl-3-phenylpropyl]-L-alanyl]-aminomethyl]-7-sulfamoyl-2H—1,2,4-benzothiadiazine-1,1-dioxide |
| XXIII | 6-Chloro-3,4-dihydro-3-[N—(carboxy-methyl)-N—[N'—[1-carboxy-3-phenyl-propyl]-L-alanyl]-aminomethyl]-7-sulfamoyl-2H—1,2,4-benzothiadiazine-1,1-dioxide hydrochloride |
| XXIV | 6-Chloro-3,4-dihydro-3-[[N—(carboxy-methyl)-N—[N'—[1-carboxy-3-phenyl-propyl]-L-alanyl]-3'-amino]propyl]-7-sulfamoyl-2H—1,2,4-benzothiadiazine-1,1-dioxide hydrochloride |

EXAMPLE XXV

6-Chloro-3,4-dihydro-3-[[N-(carboxymethyl)-N-[Nα-[1-carboxy-3-phenylpropyl]-L-lysyl]-amino]methyl]-7-sulfamoyl-2H-1,2,4,-benzothiadiazine-1,1-dioxide dihydrochloride:

To a solution of N-α-(2,2,2-trichloroethoxycarbonyl)-N-α-[(1S)-1-(ethoxycarbonyl)-3-phenylpropyl]-N-ε-carbobenzyloxy-L-lysine (7.36 g, 11.4 mmol) in 75 ml methylene chloride was added oxalyl chloride (4.97 ml, 57.0 mmol) and N,N-dimethylformamide (5 μL). The mixture was stirred 4 hours and the volatiles were removed in vacuo. The residue was diluted with anhydrous toluene (2×20 ml) and the volatiles were removed in vacuo. To the residue in 25 ml methylene chloride at 0° C. was added dropwise a solution of N-(2,2-diethoxyethyl)glycine ethyl ester (3.0 g, 13.7 mmol) and triethylamine (8.0 ml, 57.5 mmol) in 25 ml methylene chloride. The mixture was slowly warmed to room temperature, stirred overnight, diluted with water and ethyl acetate. The aqueous layer was extracted with ethyl acetate.

The combined organic layers were washed with water and brine and dried (MgSO4). Removal of the volatiles in vacuo left a residue which was purified by HPLC using 26% ethyl acetate in hexanes as the eluent. The product rich fractions were combined and the volatiles were removed in vacuo which provided 7.87 g (82%) of the oily product (XXV-A), N-(2,2-diethoxyethyl)-N-[N-α-(2,2,2-trichloroethoxycarbonyl)-N-α-[(1S)-1-(ethoxycarbonyl)-3-phenylpropyl]-N-ε-carbobenzyloxy-L-lysyl]glycine ethyl ester.

To a solution of compound (XXV-A), (7.87 g, 9.29 mmol) in 30 ml ethanol was added 1-amino-3-chloro-4,6-benzene-disulfonamide (2.65 g, 9.29 mmol) and 25 ml of ethanol saturated with gaseous HCl. The mixture was stirred 75 minutes and the volatiles were removed in vacuo. The residue was diluted with ethyl acetate, washed with water and brine, and dried (MgSO4). Removal of the volatiles in vacuo left a residue which was purified by HPLC using 55% ethyl acetate in hexanes as the eluent. The product rich fractions were combined. The volatiles were removed in vacuo which provided 5.0 g (51%) of the oily product (XXV-B), 6-chloro-3,4--dihydro-3-[N-[ethoxycarbonylmethyl]-N-[Nα-(1-ethoxycarbonyl-3-phenylpropyl)-Nα-(2,2,2-trichloroethoxycarbonyl)-Nε-(benzyloxycarbonyl)lysyl]-aminomethyl]-7-sulfamoyl-2H-1,2,4-benzothiadiazine-1,1-dioxide.

To a solution of compound (XXV-B), (1.47 g, 1.41 mmol) in 15 ml methylene chloride at 0° C. was added acetic acid (0.808 ml, 14.1 mmol) and zinc dust (0.923 g, 14.1 mmol). The mixture was warmed to room temperature and stirred 3 hours and filtered through celite. Gaseous HCl was added to the filtrate and the volatiles were removed in vacuo. The residue was dissolved in 20 ml ethanol and 19.1 ml of 1N sodium hydroxide. The mixture was stirred overnight, cooled in an ice bath, acidified with aqueous HCl to pH 1, and extracted thoroughly with ethyl acetate. The combined organic layers were washed with water and brine, and dried (MgSO4), and the volatiles were removed in vacuo. The residue was purified by trituration in ethyl acetate which provided the solid product. This material was suspended in 5 ml of methylene chloride at 0° C. and 0.5 ml of 36% HBr in acetic acid was added dropwise. The mixture was warmed to room temperature and was stirred 2 hours and diluted with ether. The precipitate was collected by filtration. Purification of the solid by trituration in chloroform provided the crystalline product (mp 167° C. (dec)).

EXAMPLE XXVI

N-carbobenzyloxy-L-alaninal dimethyl acetal

To a solution of N-carbobenzyloxy-L-alanine methyl ester (41.0 g, 0.71 mol) in 300 ml anhydrous toluene at −78° C., under N2, was added dropwise a toluene solution of diisobutyl-aluminum hydride (25% wt. % soln., 234 ml, 0.345 mol) over 0.5 hour. After the addition was complete the mixture was stirred 0.75 hour and quenched with the dropwise addition of 2N HCl (350 ml). The solution was warmed to room temperature and extracted with ethyl acetate. The combined organic layers were washed with brine and dried (MgSO4) and concentrated in vacuo. The residue was dissolved in 400 ml methanol and trimethylorthoformate (43 ml, 0.40 mol) and p-toluenesulfonic acid (0.723 g 3.8 mmol) was added. The mixture was stirred overnight and concentrated in vacuo to approximately 70% of the original volume. The residue was poured onto 800 ml of saturated NaHCO3. Ether and water were added. The aqueous layer was extracted with ether. The combined organic layers were washed with brine and dried (MgSO4) and concentrated in vacuo. Chromatography of the residue on HPLC using 30% ethyl acetate in hexanes as eluents provided the oily product N-carbobenzyloxy-L-alaninal dimethyl acetal.

N-(ethoxycarbonylmethyl)-L-alaninal dimethyl acetal

To a solution of N-carbobenzyloxy-L-alaninal dimethyl acetal (18.0 g, 71.1 mmol) in 75 ml absolute ethanol was added one drop of acetic acid and 10% palladium on carbon (3.5 g). The mixture was hydrogenated at 30 psi on a Parr Hydrogenator for 2 hours and an additional one drop of acetic acid and 10% palladium on carbon (1.5 g) were added. The mixture was hydrogenated at 30 psi for 1 hour and filtered over celite. Removal of the ethanol by distillation gave a residue which was dissolved in 50 ml of anhydrous THF and triethylamine (8.9 ml, 63.9 mmol). To the solution, cooled with an ice bath and under N2, was added dropwise a solution of ethyl bromoacetate (11.3 g, 67.9 mmol) in 20 ml anhydrous THF. The solution slowly warmed to room temperature while stirring overnight. The mixture was filtered and concentrated in vacuo. The residue was diluted with ethyl acetate, washed with aqueous NaHCO3, brine and dried (MgSO4) and concentrated in vacuo. Chromatography of the residue on HPLC, using 30% ethyl acetate in hexanes as eluents, provided 2.17 g (15%) of the oily product N-(ethoxycarbonylmethyl)-L-alaninal dimethyl acetal.

N-[N-[(1S)-1-(ethoxycarbonyl)-3-phenylpropyl]-N-(2,2,2-trichloroethoxycarbonyl)-L-alanyl]-N-(2S)-1,-1-dimethoxyprop-2-yl]glycine ethyl ester To a solution of N-[(1S)-1-(ethoxycarbonyl)-3-phenylpropyl]-N-(2,2,2-trichloroethoxycarbonyl)-L-alanine (2.44 g, 5.4 mmol) in 20 ml methylene chloride was added oxalyl chloride (2.34 ml, 27 mmol) and N,N-dimethylformamide (15 µL). The solution was stirred 1.5 hours and concentrated in vacuo. The residue was dissolved in 10 ml methylene chloride and cooled with an ice bath while under $N_2$. To this solution was added portionwise a solution of N-(ethoxycarbonylmethyl)-L-alaninal dimethyl acetal (2.87 g, 14.0 mmol) and triethylamine (5.8 ml, 41.7 mmol) in 20 ml methylene chloride. After the addition was complete the mixture was stirred overnight while slowly warming to room temperature and was poured onto ethyl acetate and water. The aqueous layer was extracted with ethyl acetate. The combined organic layers were washed with $H_2O$, brine and dried ($MgSO_4$) and concentrated in vacuo. Chromatography of the residue on HPLC using 15% ethyl acetate in hexanes as eluents provided 8.01 gm (89%) of the oily product (XXVI-A), N-[N-[(1S)-1-(ethoxycarbonyl)-3-phenylpropyl]-N-(2,2,2-trichloroethoxycarbonyl)-L-alanyl]-N-(2S)-1,-1-dimethoxyprop-2-yl]glycine ethyl ester.

N-1'-[(2'S)-6-chloro-7-sulfamoyl-3,4-dihydro-1,1-dioxide-2H-1,2,4-benzothiadiazin-3-yl]-ethyl]-N-[N-[(1S)-1-(ethoxycarbonyl)-3-phenylpropyl]-N-(2,2,2-trichloroethoxycarbonyl)-L-alanyl]glycine ethyl ester To a mixture of compound (XXVI-A) (8.01 g, 12.5 mmol) and 1-amino-3-chloro-4,6-benzene disulfonamide (3.6 g, 12.5 mmol) in 35 ml absolute ethanol was added dropwise 30 ml of ethanol saturated with gaseous HCl. The resulting solution was stirred at room temperature for 2 hours and concentrated in vacuo. The residue was dissolved in ethyl acetate, washed with water and brine and dried ($MgSO_4$) and concentrated in vacuo. Chromatography of the residue on HPLC using 42% ethyl acetate in hexanes provided 2.24 g (21%) of product (XXVI-B), N-1'-[(2'S)-6-chloro-7-sulfamoyl-3,4-dihydro-1,1-dioxide-2H-1,2,4-benzothiadiazin-3-yl]-ethyl]-N-[N-[(1S)-1-(ethoxycarbonyl)-3-phenylpropyl]-N-(2,2,2-trichloroethoxycarbonyl)-L-alanyl]glycine ethyl ester.

N-[1'-[(2'S)-6-chloro-7-sulfamoyl-3,4-dihydro-1,-1-dioxide-2H-1,2,4-benzothiadiazin-3-yl]-ethyl]-N-[N-[(1S)-1-(ethoxycarbonyl)-3-phenylpropyl]-L-alanyl]glycine ethyl ester hydrochloride To a solution of compound (XXVI-B) (3.0 g, 3.5 mmol in 15 ml glacial acetic acid was added zinc dust (8.0 g, 0.122 mol). The mixture was stirred under $N_2$ for 1 hour and filtered over celite. Gaseous HCl was added to the filtrate and the solution concentrated in vacuo. The residue was chromatographed via HPLC using 40% ethyl acetate and 5% ethanol in hexanes as eluents. The product rich fractions were treated with gaseous HCl and concentrated in vacuo which provided 1.58 g (63%) of the crystalline product, N-[1'-[(2'S)-6-chloro-7-sulfamoyl-3,4-dihydro-1,-1-dioxide-2H-1,2,4-benzothiadiazin-3-yl]-ethyl]-N-[N-[(1S)-1-ethoxycarbonyl)-3-phenylpropyl]-L-alanyl]glycine ethyl ester hydrochloride (XXVI-C).

N-[1'[(2'S)-6-chloro-7-sulfamoyl-3,4-dihydro-1,-1-dioxide-2H-1,2,4-benzothiadiazin-3-yl]-ethyl]-N-[N-[(1S)-1-carboxy)-3-phenylpropyl]-L-alanyl]glycine hydrochloride To a solution of compound (XXVI-C) (1.0 g, 1.48 mmol) in 20 ml ethanol was added aqueous sodium hydroxide (14.8 ml of 1N solution, 14.8 mmol). The solution was stirred overnight at room temperature, cooled with an ice bath, acidified to pH 1 with aqueous HCl, and extracted with ethyl acetate. The combined organic extracts were washed with $H_2O$, brine and dried ($MgSO_4$) and concentrated in vacuo. The residue was triturated with 50% ether in ethyl acetate which provided 0.8 g (81%) of the crystalline product (XXVI-D), m.p. 178°-180° C.: N-[1'[(2'S)-6-chloro-7-sulfamoyl-3,4-dihydro-1,-1-dioxide-2H-1,2,4-benzothiadiazin-3-yl]-ethyl]-N-[N-[(1S)-1-carboxy)-3-phenylpropyl]-L-alanyl]glycine hydrochloride.

EXAMPLE XXVII

N-Methyl-N-(2,2-dimethoxyethyl)nitrosoamine

A solution of 1-(methylamino)-2,2-dimethoxyethane (132.6 g; 1.11 mol) and pyridine (94.5 ml; 1.17 mol) in THF (1.3 ) was brought to 0°-5° C. with an ice-bath and nitrosonium tetrafluoroborate (139.5 g; 1.19 mol) was added in portions over 35 minutes. Fuming was observed and the temperature of the reaction mixture was kept below 20° C. throughout the addition. After stirring an additional 20 minutes, the white solid which had formed (pyridinium tetrafluoroborate) was filtered and $CH_2Cl_2$ and $H_2O$ were added. The organic phase was washed a second time with $H_2O$, dried (anhyd. $Na_2CO_3$) and concentrated in vacuo at 40° C. to yield an amber oil. This oil was distilled at vacuum pump pressure (2-4 mm Hg) to yield Compound (XXVII-A), N-Methyl-N-(2,2-dimethoxyethyl)nitrosoamine (73.0 g; 44%) as a yellow liquid: bp 75°-85° C. Both TLC and NMR indicated a mixture of Z and E isomers.

A solution of compound (XXVII-A) (6.4 g; 0.044 mol) in THF (120 ml) was added dropwise to a suspension of lithium aluminum hydride (4.0 g; 0.106 mol) in THF (150 ml) over 40 minutes. An exotherm was observed during the course of the addition, raising the temperature from 33° C. to 40° C. The reaction mixture was stirred at room temperature for 40 minutes and then refluxed for 40 minutes. After cooling overnight, 120 ml of 30% NaOH was added cautiously, keeping the temperature below 50° C. Two extractions with EtOAc gave, after drying (anhyd. $Na_2CO_3$) and concentration in vacuo at 40° C., the crude product. Vacuum distillation at about 30-40 mm Hg gave pue (XXVII-B), N-Methyl-N-(2,2-dimethoxy-ethyl)hydrazine (4.4 g; 75%) as a very pale yellow oil: bp 97°-101° C., Both TLC and NMR confirmed the product to be pure.

N-Methyl-N-(2,2-dimethoxyethyl)-N'-[N-(1S)-ethoxycarbonyl-3-phenylpropyl-L-alanyl]hydrazine To a solution of N-[1-ethoxycarbonyl-3-phenylpropyl]-L-alanine (4.6 g; 0.016 mol) in THF (110 ml) was added 1,1-carbonyldiimidazole (2.8 g; 0.017 mol). After stirring for 5 minutes at room temperature, compound (XXVII-B) (2.2 g; 0.016 mol) was added and the reaction mixture was stirred at room temperature overnight. Concentration in vacuo at 40° C. yielded a golden oil. Column chromatography (silica gel 60 (70-230 mesh), elution with EtOAc:MeOH=7:3) gave pure N-methyl-N-(2,2-dimethoxyethyl)-N'-[N-(1S)-ethoxycarbonyl-3-phenylpropyl-L-alanyl]hydrazine (XXVII-C) (2.5 g; 39%) as a viscous yellow oil. TLC and NMR confirmed product purity.

N-Methyl-N-(2,2-dimethoxyethyl)-N'-[N-(1S)-ethoxycarbonyl-3-phenylpropyl-L-alanyl]-N'-(t-butoxycarbonylmethyl)hydrazine A solution of (XXVII-C) (2.0 g; 5.06 mmol) in THF (16 ml) was cooled in an ice bath and t-butyl bromoacetate (7.9 g; 40.5 mmol) was added. After 5 minutes, sodium hydride (60% in mineral oil; 0.6 g; 15.0 mmol) was added. Vigorous gas evolution was observed. The reaction mixture was brought to room temperature slowly overnight. Ethyl acetate and H₂O were added cautiously and the organic phase was dried (anhyd. Na₂CO₃) and concentrated in vacuo at 40° C. to yield a maroon oil. Column chromatography (silica gel 60 (70-230 mesh), elution with EtOAc) gave pure N-Methyl-N-(2,2-dimethoxyethyl)-N'-[N-(1S)-ethoxycarbonyl-3-phenylpropyl-L-alanyl]-N'-(t-butoxycarbonylmethyl)hydrazine (XXVII-D) (1.3 g; 50%) as a viscous yellow oil.

3-[N-Methyl-N'-[N-[(1S)-ethoxycarbonyl-3-phenylpropyl]-L-alanyl]-N'-(t-butoxycarbonylmethyl)]hydrazinylmethyl-6-chloro-3,4-dihydro-2H-1,2,4-benzothiadiazine-7-sulfonamide 1,1-dioxide (XXVII-E)

To a solution of (XXVII-D) (7.3 g; 0.014 mol) in acetonitrile (68 g) was added 2,4-disulfamoyl-5-chloroaniline (7.3 g; 0.026 mol) followed by concentrated HCl (7.3 g) and H₂O (17 g). The suspension was warmed to 30°-35° C. for 3 hours and then left at room temperature overnight. Sodium bicarbonate (10.0 g) was added and the reaction mixture was stirred for 15 minutes. The phases were then separated and the organic phase was concentrated in vacuo. The residue was taken up on CHCl₃ (120 ml; unreacted 2,4-disulfamoyl-5-chloroaniline remains insoluble) and dried (anhyd. MgSO₄). Concentration in vacuo gave crude 3-[N-methyl-N'-[N-[(1S)-ethoxycarbonyl-3-phenylpropyl]-L-alanyl]-N'-(t-butoxycarbonylmethyl)]hydrazinylmethyl-6-chloro-3,4-dihydro-2H-1,2,4-benzothiadiazine-7-sulfonamide-1,1-dioxide (XXVII-E) (9.5 g). Column chromatography (silica gel 60 70-230 mesh), elution with EtOAc:hexane=4:1) gave pure (XXVII-E) (4.0 g; 38%).

3-[N-Methyl-N'-[N-[(1S)-ethoxycarbonyl-3-phenylpropyl]-L-alanyl]-N'-carboxymethyl]hydrazinylmethyl-6-chloro-3,4-dihydro-2H-1,2,4-benzothiadiazine-7-sulfonamide 1,1-dioxide A solution of (XXVII-E) (2.0 g; 2.73 mmol) in dioxane (5 ml) was prepared. A solution of HCl gas (27.7 g) in dioxane (60 g) was prepared separately at 4° C. and the two solutions were mixed. After 45 minutes, N₂ was passed into the reaction mixture, evaporating 31 g of solvent. Hexanes (60 ml) were added and then the solvent was decanted from the precipitate. This was repeated twice more. Drying in vacuo at 50° C. gave impure (XXVII-F), 3-[N-methyl-N'-[N-[(1S)-ethoxycarbonyl-3-phenylpropyl]-L-alanyl]-N'-carboxymethyl]hydrazinylmethyl-6-chloro-3,4-dihydro-2H-1,2,4-benzothiadiazine-7-sulfonamide 1,1-dioxide free of impurities but contaminated with silica gel, which could be removed by the following procedure. Contaminated (XXVII-F) (1.3 g; 1.83 mmol) was dissolved in absolute EtOH (50 ml) and filtered through celite. Concentration in vacuo to about 5 ml in volume induced crystallization. Addition of hexanes (50 ml) further aided crystallization. After stirring for 1 hour, the precipitate was collected, washed with hexanes and dried at 65° C. for 2 hours under high vacuum to yield pure (XXVII-F) (1.2 g; 62% from XX-E): mp 170°-172° (d). The compound is pure by TLC and NMR. Analytical HPLC indicated a 1:1 mixture of SSS and SSR diastereomers. Combustion analysis as well as chloride analysis indicated 1.5 moles of HCl present.

EXAMPLE XXVIII

N-(2,2,2-trichloroethoxycarbonyl)-L-leucine

Eighty grams (0.44 mole) of L-leucine methyl ester hydrochloride were dissolved in 400 ml of water. One hundred grams of sodium bicarbonate were added portionwise followed by 100 ml of ethyl acetate. One hundred grams (0.47 mole) of trichloroethyl chloroformate were added dropwise over a period of ½ hour while the temperature was maintained at about 15° C. by means of a cold water bath. After the addition was complete, the cooling bath was removed and the mixture was stirred for 2 hours at room temperature. Ethyl acetate (200 ml) was added and the layers were separated. The organic phase was washed with 100 ml of dilute hydrochloric acid and twice with 100 ml of brine. The ethyl acetate solution was then dried with anhydrous magnesium sulfate and the solvent was removed on a rotary evaporator. The residue (146 g) was distilled under vacuum, b.p. 130°-140° C. at 0.2 mm Hg. Yield: 131.3 g (92.6%) of N-(2,2,2-trichloro-ethoxycarbonyl)-L-leucine as a colorless oil.

(N-(2,2,2-trichloroethoxycarbonyl)-L-leucinealdehyde)

96.5 grams (0.3 mole) of N-(2,2,2-trichloroethoxycarbonyl)-L-leucine were dissolved in 565 ml of toluene. The mixture was cooled to −65° C. in a methanol/dry ice bath and 30 ml of 1.5M solution of diisobutylaluminum hydride (DIBAL) in toluene were added dropwise over a period of 45 minutes while the temperature was maintained at −60° to −65° C. After the addition was complete, the reaction mixture was stirred for 1 hour at about −65° C. It was then warmed up to about −50° C. and stirred for 15 minutes. A solution of 261 g of concentrated hydrochloric acid in 1 L of water was added carefully. The mixture was stirred for 10 minutes and the layers were separated. The organic phase was washed with 500 ml of deionized water, dried with anhydrous magnesium sulfate, and the solvent was stripped on a rotary evaporator at 60° C. under reduced pressure to yield 87 g of a colorless oil. The crude product thus obtained, (N-(2,2,2-trichloroethoxycarbonyl)-L-leucinealdehyde), the purity of which was estimated to be about 60% based on the NMR spectrum, was used in the next reaction step without further purification.

83 grams of crude N-(2,2,2-trichloroethylcarbonyl)-L-leucinealdehyde (0.17 mole based on 60% assay) were dissolved in 500 ml of ethanol. Para-toluenesulfonic acid monohydrate (10 g) and 50 g (0.17 mole) of 1-amino-3-chloro-4,6-benzenedisulfonamide were added and the suspension was heated to reflux for 5 hours. The mixture was then cooled to room temperature and the solids were filtered off. The filter cake was washed with 500 ml of ethanol and dried in a vacuum oven at 80° C. Yield: 74.5 g (76%) of compound (XXVII-A), 1-(2,2,2-trichloroethoxycarbonylamino)-1-(6-chloro-3,4-dihydro-7-sulfamoyl-2H-1,2,4-benzothiadiazin-3-yl)-3-methylbutane, m.p. 265°-267° C. (dec.).

The mixture of (XXVIII-A) (69.2 g) in 700 ml of THF, 120 ml of acetic acid, zinc dust (60 g) was stirred at room temperature overnight. After filtration, the filtrate was concentrated to dryness and triturated with 1000 ml of ether. The solid was collected with filtration, dried and treated with dilute hydrochloric acid solution. The mixture was filtered and the filtrate was treated with sodium bicarbonate to bring the pH to about 5. The mixture was extracted with ethyl acetate and the extracts evaporated to dryness to obtain 12 g of crude 1-amino-1-(6-chloro-3,4-dihydro-7-sulfamoyl-2H-1,2,4-benzothiadiazin-3-yl)-3-methylbutane (XXVIII-B). This material was dissolved in 100 ml of methanol and filtered with charcoal. Water (100 ml) was added to the filtrate, the mixture was heated briefly to reflux, then cooled down to room temperature and filtered. After drying, 6 g of (XXVIII-B) were obtained as an approximately 1:1 mixture of two diastereomers.

The mixture of (XXVIII-B) (7.85 g), $K_2CO_3$ (5.67 g) and t-butyl bromoacetate (7 g) in 78 ml of DMSO was stirred at room temperature for 15 hours. After filtration, the filtrate was poured into 100 ml of water, extracted with ethyl acetate (3×100 ml). The combined organic solution was concentrated to dryness and triturated with 50 ml of ether. The solid was collected by filtration and purified by column chromatography eluting with EtOAc/toluene/MeOH (45:45:5) to give 2.7 g of a mixture of two diastereomers of 1-((tert-butoxycarbonylmethyl)amino)-1-(6-chloro-3,4-dihydro-7-sulfamoyl-2H-1,2,4-benzothiadiazin-3-yl)-3-methylbutane (XXVIII-C).

1.51 g of N-(1-ethoxycarbonyl-3-phenylpropyl)-N-(2,2,2-trichloroethoxycarbonyl)-L-alanine in 15 ml of $CH_2Cl_2$ was added with 0.48 g of oxalyl chloride, 3 drops of DMF and stirred at room temperature for 2 hours. After evaporation to dryness using a rotary evaporator, the resulting acid chloride was dissolved in 15 ml of $CH_2Cl_2$ and cooled to 0° C. and added with 1.65 g of (XXVIII-C) in 5 ml of $CH_2Cl_2$ and 0.27 ml of pyridine at 0°-5° C. After stirring at room temperature for 10 hours, the reaction mixture was diluted with 80 ml of $CH_2Cl_2$, washed with $H_2O$, brine, dried ($MgSO_4$), concentrated to dryness and triturated with a mixture of ether and heptane (2:1). The solid was collected and purified by column chromatography eluting with EtOAc plus $CCl_4$ (3:7) to give 1 g of N-[N'-(1-ethoxycarbonyl-3-phenylpropyl)-N'-(2,2,2-trichloroethoxycarbonyl)-L-alanyl]-N-[1'-(6-chloro-3,4-dihydro-7-sulfamoyl-2H-1,2,4-benzothiadiazin-3-yl)-3'-(methyl)butyl]glycine-tert-butyl ester (XXVIII-D) as a mixture of two diastereomers.

The mixture of (XXVIII-D) (9 g) in 100 ml of THF, acetic acid (20 ml), and zinc dust (5.3 g) was stirred at room temperature overnight. After filtration, the filtrate was concentrated to dryness and triturated with 100 ml of ether. The resulting solid was collected and purified by column chromatography eluting with EtOAc plus $CCl_4$ (3:2) to give 4 g of (XXVIII-E), N-[N'-(1-ethoxycarbonyl-3-phenylpropyl)-L-alanyl]-N-[1'-(6-chloro-3,4-dihydro-7-sulfamoyl-2H-1,2,4-benzothiadiazin-3-yl)-3'-(methyl)butyl]glycine tert-butyl ester.

1.3 g of (XXVIII-E) in 3 ml of dioxane was added with gaseous HCl (18.28 g)/dioxane (39 ml) dropwise at 3° C. over 15 minutes. After stirring at 12°-18° C. for 45 minutes, the mixture was concentrated using rotary evaporation and then high vacuum pump. The resulting residue was then triturated with 80 ml of ether. The collected solid was redissolved in 100 ml of EtOH and filtered to remove traces of insoluble material. The filtrate was finally concentrated to about 5 ml content and triturated with 30 ml of ether. The solid was collected and dried at 40° C. under high vacuum to give 0.73 g of (XXVIII-F), N-[N'-(1-ethoxycarbonyl-3-phenylpropyl)-L-alanyl]-N-[1'-(6-chloro-3,4-dihydro-7-sulfamoyl-2H-1,2,4-benzothiadiazin-3-yl)-3'-(methyl)butyl]glycine hydrochloride.

EXAMPLE XXIX

N-[N'-(1-carboxy-3-phenylpropyl)-L-alanyl]-N-[(1'-(6-chloro-3,4-dihydro-7-sulfamoyl-2H-1,2,4-benzothiadiazin-3-yl)-3'-methyl)butyl]glycine

EXAMPLE XXX

N-[Nα-(1-carboxy-3-phenylpropyl)-Nε-(benzyloxycarbonyl)-L-lysyl]-N-[(6-chloro-3,4-dihydro-7-sulfamoyl-2H-1,2,4-benzothiadiazin-1,1-dioxo-3-yl)-methyl]glycine (SSR)

EXAMPLE XXXI

N-[Nα-(1-carboxy-3-phenylpropyl)-Nε-(benzyloxycarbonyl)-L-lysyl]-N-[(6-chloro-3,4-dihydro-7-sulfamoyl-2H-1,2,4-benzothiadiazin-1,1-dioxo-3-yl)-methyl]glycine (SSS)

What is claimed is:

1. Compounds having the formula

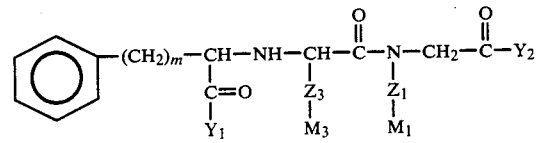

and pharmaceutically acceptable salts thereof, wherein
m is 1 or 2;
$Y_1$ and $Y_2$ are independently hydroxy, alkoxy containing 1 to 6 carbon atoms or benzyloxy,
$Z_1M_1$ is

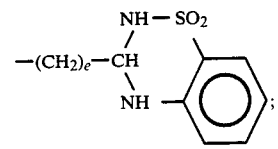

e is 1–4;
$Z_3$ is alkyl containing 1 to 6 carbon atoms; and
$M_3$ is

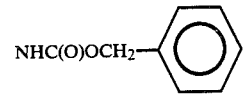

2. A compound or salt of claim 1 wherein there is at least one asymmetric carbon, and the substituents on each asymmetric carbon are in the "S" configuration.

3. A pharmaceutical preparation having angiotensin converting enzyme inhibitory activity comprising an angiotensin converting enzyme inhibitory amount of a compound or salt according to claim 1 in association with a pharmaceutically acceptable carrier.

4. The method of alleviating hypertension in a mammal in need of treatment therefor, comprising administering to said mammal an antihypertensive effective amount of one or more compounds or salts according to claim 1.

5. The compound N-[Nα-(1-carboxy-3-phenylpropyl)-Nε-(benzyloxycarbonyl)-L-lysyl]-N-[(6-chloro-3,4-dihydro-7-sulfamoyl-2H-1,2,4-benzothiadiazin-1,1- dioxo-3-yl)-methyl]glycine (SSR) and its pharmaceutically acceptable salts.

6. The compound N-[Nα-(1-carboxy-3-phenylpropyl)-Nε-(benzyloxycarbonyl)-L-lysyl]-N-[(6-chloro-3,4-dihydro-7-sulfamoyl-2H-1,2,4-benzothiadiazin-1,1-dioxo-3-yl)-methyl]glycine (SSS) and its pharmaceutically acceptable salts.

* * * * *